(12) United States Patent
Turner et al.

(10) Patent No.: US 7,170,050 B2
(45) Date of Patent: Jan. 30, 2007

(54) APPARATUS AND METHODS FOR OPTICAL ANALYSIS OF MOLECULES

(75) Inventors: Stephen Turner, Palo Alto, CA (US); Jonas Korlach, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 10/944,106

(22) Filed: Sep. 17, 2004

(65) Prior Publication Data

US 2006/0060766 A1 Mar. 23, 2006

(51) Int. Cl.
*H05H 3/04* (2006.01)
*G02B 6/00* (2006.01)
*G02B 6/10* (2006.01)

(52) U.S. Cl. ............ 250/251; 250/227.14; 250/227.11; 385/129; 385/141; 385/142; 385/144

(58) Field of Classification Search ............ None
See application file for complete search history.

(56) References Cited

U.S. PATENT DOCUMENTS

| | | | |
|---|---|---|---|
| 4,994,373 A | 2/1991 | Stavrianopoulos et al. |
| 5,001,050 A | 3/1991 | Blanco et al. |
| 5,198,543 A | 3/1993 | Blanco et al. |
| 5,200,313 A | 4/1993 | Carrico |
| 5,243,618 A | 9/1993 | Dolezal et al. |
| 5,302,509 A | 4/1994 | Cheeseman |
| 5,403,708 A | 4/1995 | Brennan et al. |
| 5,405,747 A | 4/1995 | Jett et al. |
| 5,465,151 A | 11/1995 | Wybourne et al. |
| 5,470,710 A | 11/1995 | Weiss et al. |
| 5,547,835 A | 8/1996 | Koster |
| 5,601,982 A | 2/1997 | Sargent et al. |
| 5,620,854 A | 4/1997 | Holzrichter et al. |
| 5,631,134 A | 5/1997 | Cantor |
| 5,646,264 A | 7/1997 | Glazer et al. |
| 5,661,028 A | 8/1997 | Foote |
| 5,677,196 A | 10/1997 | Herron et al. |
| 5,677,769 A | 10/1997 | Bendett |
| 5,688,648 A | 11/1997 | Mathies et al. |
| 5,695,934 A | 12/1997 | Brenner |
| 5,703,222 A | 12/1997 | Grossman et al. |

(Continued)

FOREIGN PATENT DOCUMENTS

EP 0745686 A1 12/1996

(Continued)

OTHER PUBLICATIONS

Chatterjee, et al., "Cloning and overexpression of the gene encoding bacteriophage T5 DNA polymerase," *Gene*. 1991; 97:13-19.

(Continued)

*Primary Examiner*—Nikita Wells
(74) *Attorney, Agent, or Firm*—Wilson Sonsini Goodrich & Rosati

(57) ABSTRACT

The present invention relates to optical confinements, methods of preparing and methods of using them for analyzing molecules and/or monitoring chemical reactions. The apparatus and methods embodied in the present invention are particularly useful for high-throughout and low-cost single-molecular analysis.

20 Claims, 14 Drawing Sheets

U.S. PATENT DOCUMENTS

| | | | |
|---|---|---|---|
| 5,846,727 A | 12/1998 | Soper et al. | |
| 5,854,033 A | 12/1998 | Lizardi | |
| 5,858,671 A | 1/1999 | Jones | |
| 5,922,591 A | 7/1999 | Anderson et al. | |
| 5,961,923 A | 10/1999 | Nova et al. | |
| 6,004,744 A | 12/1999 | Goelet et al. | |
| 6,027,890 A | 2/2000 | Ness et al. | |
| 6,048,690 A | 4/2000 | Heller et al. | |
| 6,210,896 B1 | 4/2001 | Chan | |
| 6,221,592 B1 | 4/2001 | Schwartz et al. | |
| 6,232,075 B1 | 5/2001 | Williams et al. | |
| 6,255,083 B1 | 7/2001 | Williams et al. | |
| 6,263,286 B1 | 7/2001 | Gilmanshin et al. | |
| 6,280,939 B1 | 8/2001 | Allen | |
| 6,287,824 B1 | 9/2001 | Lizardi | |
| 6,306,607 B2 | 10/2001 | Williams et al. | |
| 6,323,009 B1 | 11/2001 | Lasken et al. | |
| 6,325,553 B1* | 12/2001 | Deacon et al. | 385/89 |
| 6,355,420 B1 | 3/2002 | Chan | |
| 6,399,335 B1 | 6/2002 | Kao et al. | |
| 6,403,311 B1 | 6/2002 | Chan | |
| 6,485,944 B1 | 11/2002 | Church et al. | |
| 6,510,263 B1 | 1/2003 | Maisenholder et al. | |
| 6,524,829 B1 | 2/2003 | Seeger | |
| 6,528,780 B1 | 3/2003 | Mitsuoka et al. | |
| 6,573,089 B1 | 6/2003 | Vann | |
| 6,617,137 B2 | 9/2003 | Dean et al. | |
| 6,618,537 B2* | 9/2003 | Temkin et al. | 385/132 |
| 6,642,034 B2 | 11/2003 | Lizardi | |
| 6,670,126 B2 | 12/2003 | Kingsmore et al. | |
| 6,713,672 B1 | 3/2004 | Stickney | |
| 6,740,865 B1* | 5/2004 | Rushbrook et al. | 250/227.14 |
| 6,961,125 B2* | 11/2005 | Rushbrooke et al. | 356/417 |
| 2001/0014850 A1 | 8/2001 | Gilmanshin et al. | |
| 2001/0029049 A1* | 10/2001 | Walt et al. | 436/518 |
| 2002/0025529 A1 | 2/2002 | Quake et al. | |
| 2002/0110939 A1 | 8/2002 | Miki et al. | |
| 2002/0164629 A1 | 11/2002 | Quake et al. | |
| 2002/0180570 A1 | 12/2002 | Facer et al. | |
| 2003/0044781 A1 | 3/2003 | Korlach et al. | |
| 2003/0064366 A1 | 4/2003 | Hardin et al. | |
| 2003/0092034 A1 | 5/2003 | Cooper et al. | |
| 2003/0123827 A1* | 7/2003 | Salerno et al. | 385/129 |
| 2003/0137313 A1 | 7/2003 | Jannsen et al. | |
| 2003/0148542 A1 | 8/2003 | Pawlak et al. | |
| 2003/0174992 A1 | 9/2003 | Levene et al. | |
| 2003/0186255 A1 | 10/2003 | Williams et al. | |
| 2003/0194740 A1 | 10/2003 | Williams et al. | |
| 2004/0110180 A1 | 6/2004 | Recipon et al. | |
| 2004/0132155 A1 | 7/2004 | Plowman et al. | |
| 2004/0157306 A1 | 8/2004 | Plowman et al. | |
| 2004/0203097 A1 | 10/2004 | Yue et al. | |
| 2005/0196317 A1* | 9/2005 | Walt et al. | 422/57 |
| 2006/0017917 A1* | 1/2006 | Cullum et al. | 356/301 |

FOREIGN PATENT DOCUMENTS

| | | |
|---|---|---|
| EP | 0258 017 B1 | 6/1997 |
| EP | 0834 576 A2 | 4/1998 |
| WO | WO 90/13666 | 11/1990 |
| WO | WO 91/13075 | 9/1991 |
| WO | WO 93/21340 A1 | 10/1993 |
| WO | WO 95/06138 | 3/1995 |
| WO | WO 96/27025 | 9/1996 |
| WO | WO 98/44152 | 10/1998 |
| WO | WO 99/05315 | 2/1999 |
| WO | WO 99/19341 | 4/1999 |
| WO | WO 00/06770 | 2/2000 |
| WO | WO 00/09757 | 2/2000 |
| WO | WO 00/36151 | 6/2000 |
| WO | WO 00/36152 | 6/2000 |
| WO | WO 00/40750 | 7/2000 |
| WO | WO 00/53805 | 9/2000 |
| WO | WO 00/53812 | 9/2000 |
| WO | WO 00/58507 | 10/2000 |
| WO | WO 00/60072 | 10/2000 |
| WO | WO 00/60114 | 10/2000 |
| WO | WO 01/13088 A1 | 2/2001 |
| WO | WO 01/16375 A2 | 3/2001 |
| WO | WO 01/23610 | 4/2001 |
| WO | WO 01/25480 | 4/2001 |
| WO | WO 01/32930 | 5/2001 |
| WO | WO 01/57248 | 8/2001 |
| WO | WO 01/57249 | 8/2001 |
| WO | WO 01/94609 | 12/2001 |
| WO | WO 02/02813 | 1/2002 |
| WO | WO 02/03305 | 1/2002 |
| WO | WO 02/29106 | 4/2002 |
| WO | WO 02/061126 | 8/2002 |
| WO | WO 02/061127 | 8/2002 |
| WO | WO 02/072892 | 9/2002 |
| WO | WO 02/095070 | 11/2002 |
| WO | WO 02/101095 | 12/2002 |
| WO | WO 03/010289 | 2/2003 |
| WO | WO 03/016565 | 2/2003 |
| WO | WO 03/020734 | 3/2003 |
| WO | WO 03/089931 A1 | 10/2003 |

OTHER PUBLICATIONS

Craighead, H.G. "Nanoelectromechanical Systems," *Science*. 2000; 290: 1532-1535.

Davis et al., "Rapid DNA Sequencing Based Upon Single Molecule Detection," *Genetic Analysis Techniques and Applications*. 1991; 8(1):1-7.

Dobrikov, et al., "Sensitized Photomodification of Single-Stranded DNA by a Binary System of Oligonucleotide Conjugates," *Antisense & Nucleic Acid Drug Development*. 1997; 7:309-317.

Dörre, et al., "Techniques for Single Molecule Sequencing," *Bioimaging*. 1997; 5:139-152.

Dörre, K., et al., "Highly Efficient Single Molecule Detection in Microstructures," *Journal of Biotechnology*. 2001; 86(3):225-236.

Foquet, et al., "Fabrication of Microcapillaries and Waveguides for Single Molecule Detection," *SPIE*. 1998; 3258:(0277-786X) 141-147.

Harding, et al., "Single-Molecule Detection as an Approach to Paid DNA Sequencing," *Trends in Biotechnol*. 1992; 10:55-57.

Heinze, K.G., et al., "Two-photon Fluorescence Coincidence Analysis: Rapid measurements of enzyme kinetics," *Biophyscial Journal*. 2002; 83(3):1671-1681.

Jackson, John D., "Classical Elecytrodynamics," Second Edition, John Willey and Sons; 1975.

Jacobsen, et al., "The N-Terminal Amino-Acid Sequences of DNA Polymerase I from *Escherichia coli* and of the Large and the Small Fragments Obtained by a Limited Proteolysis," *Eur. J. Biochem*. 1974; 45:623-627.

Jung, et al., "Bacteriophage PRDI DNA polymerase: Evolution of DNA polymerases," *Proc. Natl. Aced. Sci. USA*. 1987; 84:8287-8291.

Kaboord, et al., "Accessory proteins function as matchmakers in the assembly of the T4 DNA polymerase holoenzyme," *Current Biology*. 1995; 5:149-157.

Kang, et al., "Investigations of Potential—Dependent Fluxes of Ionic Permeates in Gold Nanotubule Membranes Prepared Via the Template Method," *Langmuir*. 2001; 17(9):2753-2759.

Kawata, et al., "Feasibility of Molecular-Resolution Fluorescence Near-Field Microscopy Using Multi-Photon Absorption and Field Enhancement Near a Sharp Tip," *Journal of Applied Physics*. 1999; 85(3):1294-1301.

Kristensen, et al., "Rapid and Simple Preparation of Plasmids Suitable for Dideoxy DNA Sequencing and Other Purposes," *DNA Sequence*. 1991; 1:227-232.

Levene, et al., "Zero-Mode Waveguides for Single-Molecule Analysis at High Concentrations," *Science*. 2003; 299:682-686.

Lopez, et al., "Subwavelength Surface-Relief Gratings Fabricated by Microcontact Printing of Self-Assembled Monolayers," *Applied Optics*. 2001; 40(13):2068-2075.

Matsumoto, et al., "Primary structure of bacteriophage M2 DNA polymerase: conserved segments within protein-priming DNA polymerases and DNA polymerase I of *Escherichia coli*," *Gene*. 1989; 84:247-255.

McDonald, et al., "Fabrication of a Configurable, Single-Use Microfluidic Device," *Analytical Chemistry*. 2001. 73 (23):5645-5650.

Mendez, et al., "Protein-primed DNA replication: a transition between two modes of priming by a unique DNA polymerase," *The EMBO Journal*. 1997; 16 (9):2519-2527.

Nickerson, et al., "PolyPhred: Automating the Detection and Genotyping of Single Nucleotide Substitutions Using Fluorescence-Based Resequencing," *Nucleic. Acids Research*. 1997; 25 (14):2745-2751.

Novotny, et al., "Theory of Nanometric Optical Tweezers," *Physical Review Letters*. 1997; 79 (4):645-648.

Rigler, et al., "Differences in the Mechanism of Stimulation of T7 DNA Polymerase by Tow Binding Modes of *Escherichia coli* Single-stranded DNA-binding Protein," *Journal of Biological Chemistry*. 1995; 270 (15):8910-8919.

Sanchez, et al., "Near-Field Fluorescence Microscopy Based on Two-Photon Excitation with Metal Tips," *Physical Review Letters*. 1999, 82 (20):4014-4017.

Schwille, P., et al., "Dual-Color Fluorescence Cross-Correlation Spectroscopy For Multicomponent Diffusional Analysis in Solution," *Biophysical Journal*. 1997; 72:1878-1886.

Siegal, et al., "A Novel DNA Helicase from CalfThymus," *Journal of Biological Chemistry*. 1992; 267 (19):13629-13635.

Skaliter, et al., "Rolling circle DNA replication in vitro by a complex of herpes simplex virus type I-encoded enzymes," *Proc. Natl, Acad. Sci. USA*. 1994; 91:10665-10669.

Voss, et al., "Automated Cycle Sequencing with Taquenase™: Protocols for Internal Labeling, Dye Primer and "Doublex" Simultaneous Sequencing," *BioTechniques*. 1997; 23 (2):312-318.

Webb, et al., "Nonlinear magic: multiphoton microscopy in the biosciences," *Nature Biotecnology*. 2003; 21 (11):1369-1377.

Weiss, S., "Fluorescence Spectroscopy of Single Biomolecules," *Science*. 1999; 283:1676-1683.

Zhu, et al., "Purification and characterization of PRDI DNA polymerase," *Biochimica et Biophysica Acta*. 1994; 1219:267-276.

Zijderveld, et al., "Helix-Destabilizing Properties of the Adenovirus DNA-Binding Protein,"Journal of Virology. 1994; 68 (2):1158-1164.

Eggeling, et al. Monitoring Conformational Dynamics Of A Single Molecule By Selective Fluorescence Spectroscopy. *Proc. Natl. Acad. Sci. USA*. 1998; 95:1556-1561.

Goodwin, et al. Application of Single Molecule Detection to DNA Sequencing. *Nucleosides & Nucleotides*. 1997; 16(5&6): 543-550.

Ronaghi, et al. A Sequencing Method Based on Real-Time Pyrophosphate. *Science*. 1998; 281: 363, 365.

Sanger, et al. DNA sequencing with chain-terminating inhibitors. *Proc. Natl. Acad. Sci*. USA. 1997; 74(12): 5463-5467.

* cited by examiner

71

72

A B

APPARATUS AND METHODS FOR OPTICAL ANALYSIS OF MOLECULES

TECHNICAL FIELD

The present invention relates to optical confinements, methods of preparing and methods of using them for analyzing molecules and/or monitoring chemical reactions. The apparatus and methods embodied in the present invention are particularly useful for high-throughout and low-cost single-molecular analysis.

BACKGROUND OF THE INVENTION

Confinement of illumination and signal detection has long been recognized as an important tool in molecular diagnostics since the application of Fluorescence Correlation Spectroscopy (FCS). FCS involves illumination of a sample volume containing fluorophore-labeled molecules, and detection of fluctuations in fluorescence signal produced by the molecules as they diffuse into and out of the effective observation volume. The fluorescence intensity fluctuations can best be analyzed if the volume under observation contains only a small number of fluorescing molecules, and if the background signal is low. This can be accomplished by the combination of a drastically limited detection volume and a low sample concentration. The detection volume of traditional FCS is approximately 0.5 femtoliters (or $0.5 \times 10^{-15}$ liters), and is achieved through the use of a high numerical aperture microscope objective lens to tightly focus a laser beam. In this detection volume, single molecules can be isolated at concentrations of up to approximately one nanomolar. This concentration range is unacceptably low for most biochemical reactions, which have reaction constants in the micromolar range. At lower concentrations, these reactions either do not proceed acceptably fast, or behave in a qualitatively different fashion. To observe single molecules at higher concentrations, the observation volume has to be reduced to far smaller dimensions.

In recent years, the advancement in nanofabrication technology enabled the production of nanoscale devices that are integrated with electrical, optical, chemical or mechanical elements.

However, there still remains a considerable need for small, mass produced, and disposable devices that can provide optical confinements of smaller scale, and amenable to single-molecule analysis at a higher concentration. The present invention satisfies these needs and provides related advantages as well.

SUMMARY OF THE INVENTION

A principal aspect of the present invention is the design of optical devices and methods for characterizing molecules and/or monitoring chemical reactions. The devices and methods of the present invention are particularly suited for single-molecule analysis.

Accordingly, the present invention provides an array of optical confinements having a surface density exceeding $4 \times 10^4$ confinements per $mm^2$, wherein individual confinement in the array provides an effective observation volume that is less than one nanoliters ($10 \times^{-9}$ liters), preferably on the order of zeptoliters. In certain aspects, each of the individual confinement provides an effective observation volume that is less than 100 zeptoliters, or less than 50 zeptoliters, or even less than 10 zeptoliters. In other aspects, each of the individual confinement yields an effective observation volume that permits resolution of individual molecules present at a concentration that is higher than one nanomolar, or higher than 100 nanomolar, or on the order of micromolar range. In certain preferred aspects, each of the individual confinement yields an effective observation volume that permits resolution of individual molecules present at a physiologically relevant concentration, e.g., at a concentration higher than about 1 micromolar, or higher than 50 micromolar range or even higher than 100 micromolar. The array may comprise zero-mode waveguide or other nanoscale optical structures. The array of optical confinements may further comprise another array of confinements that does not yield the above-described effective observation volume or does not permit resolution of individual molecules. For example, the array of optical confinement can be coupled to a microtiter plate that has a comparable surface density.

In another embodiment, the present invention provides a method of creating a plurality of optical confinements having the aforementioned characteristics. The method involves the steps of (a) providing a substrate; and (b) forming an array of optical confinements having a surface density exceeding $4 \times 10^4$ confinements per $mm^2$, wherein the individual confinement comprises a zero-mode waveguide comprising: a cladding surrounding a core, wherein said cladding is configured to preclude propagation of electromagnetic energy of a wavelength longer than a cutoff wavelength longitudinally through the core of the zero-mode waveguide; and (c) illuminating the array with an electromagnetic radiation of a frequency less than the cutoff frequency, thereby creating the plurality of optical confinements.

In another embodiment, the present invention provides a method of creating an optical observation volume that permits resolution of individual molecules. The method involves providing a zero-mode waveguide that comprises a cladding surrounding a core, wherein said cladding is configured to preclude propagation of electromagnetic energy of a frequency less than a cutoff frequency longitudinally through the core of the zero-mode waveguide, wherein upon illuminating the zero-mode waveguide with an electromagnetic radiation of a frequency less than the cutoff frequency, the zero-mode waveguide yields an effective observation volume that permits resolution of individual molecules. In certain aspects, the effective observation volume is less than one nanoliter ($10^{-9}$ liter), preferably on the order of zeptoliters. Using the zero-mode waveguide of the present invention, one typically can obtain an effective observation volume that is less than 100 zeptoliter ($100 \times^{-21}$ liters) or less than 50 zeptoliters, or even less than 10 zeptoliters. In other aspects, the method yields an effective observation volume that permits resolution of individual molecules present at a concentration that is higher than one nanomolar, more often higher than 100 nanomolar, and preferably on the order of micromolar range. In preferred embodiments, individual molecules present at a concentration higher than about 5 micromolar, or higher than 7.5 micromolar, or even higher than 50 micromolar range, can be resolved by the method of the present invention.

The present invention also provides a method of detecting interactions among a plurality of molecules. The method comprises the steps of (a) placing the plurality of molecules in close proximity to an array of zero-mode waveguides, wherein individual waveguides in the array are separated by a distance sufficient to yield detectable intensities of diffractive scattering at multiple diffracted orders upon illuminating the array with an incident wavelength; (b) illuminating the array of zero-mode waveguides with an incident wavelength; and (c) detecting a change in the intensities of diffractive scattering of the incident wavelength at the multiple diffracted orders, thereby detecting the interactions among a plurality of molecules.

The present invention also provides a method of reducing diffractive scattering upon illuminating an array of optical confinement with an incident wavelength, wherein the array comprises at least a first optical confinement and a second confinement, said method comprising: forming the array of optical confinements wherein the first zero-mode waveguide is separated from the second zero-mode waveguide by a distance such that upon illumination with the incident wavelength, intensity of diffractive scattering resulting from the first zero-mode waveguide at a given angle is less than that if the first zero-mode waveguide were illuminated with the same incident wavelength in the absence of the second zero-mode waveguide.

Further provided by the present invention is a method of fabricating an array of optical confinements that exhibits a minimal intensity of diffractive scattering of an incident wavelength, comprising: providing a substrate; and forming the array of optical confinements on the substrate such that individual confinements in the array are separated from each other at a distance less than one half of the wavelength.

DETAILED DESCRIPTION OF THE INVENTION

Figure 1:
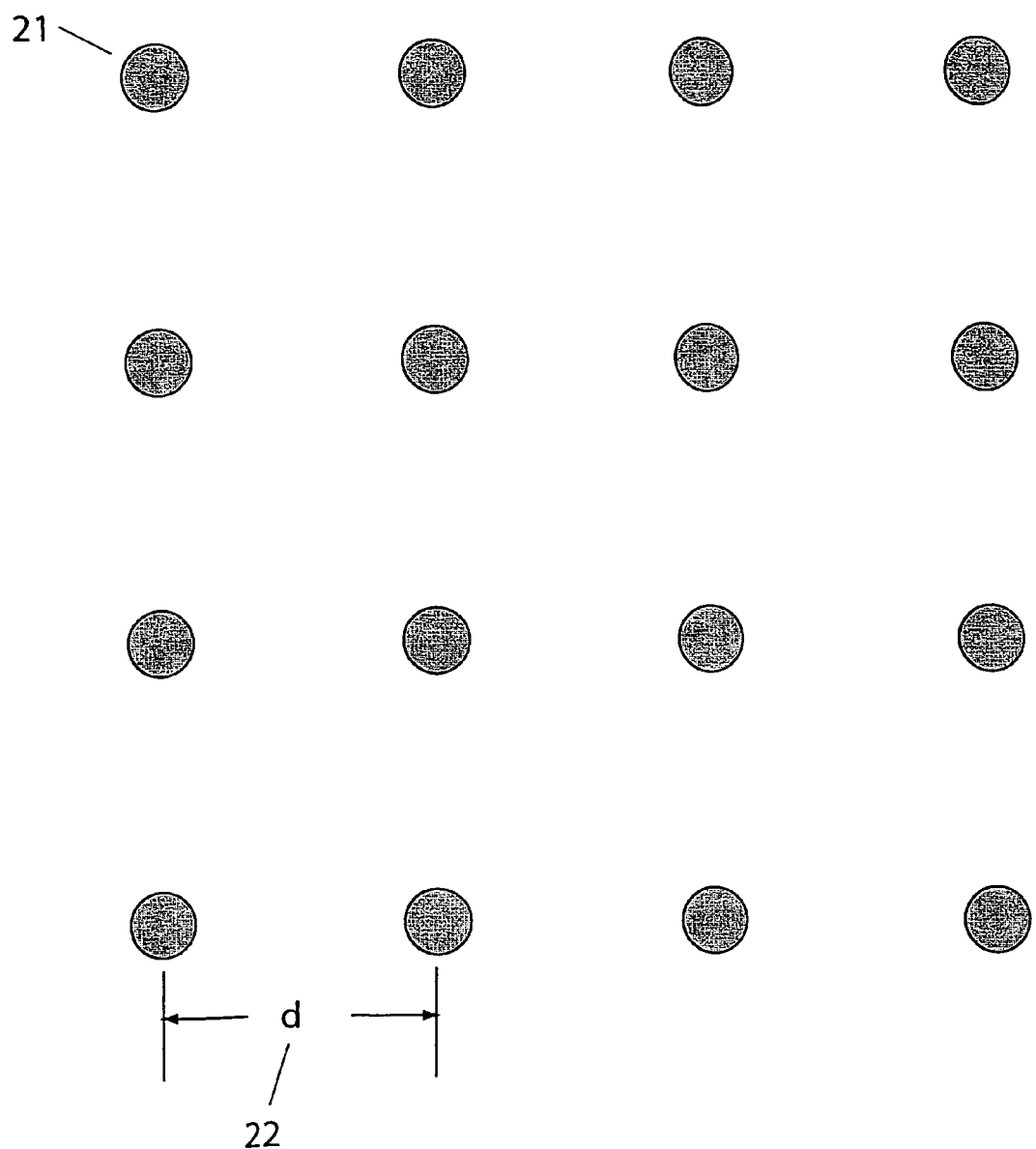
FIG. 1 depicts an array of optical confinement, here zero-mode waveguide arranged in a square format. The annotations of various components shown in the figure are as follows; 21: a zero mode waveguide. 22: "d" is the variable indicating the inter-zero mode waveguide spacing.
Figure 2:
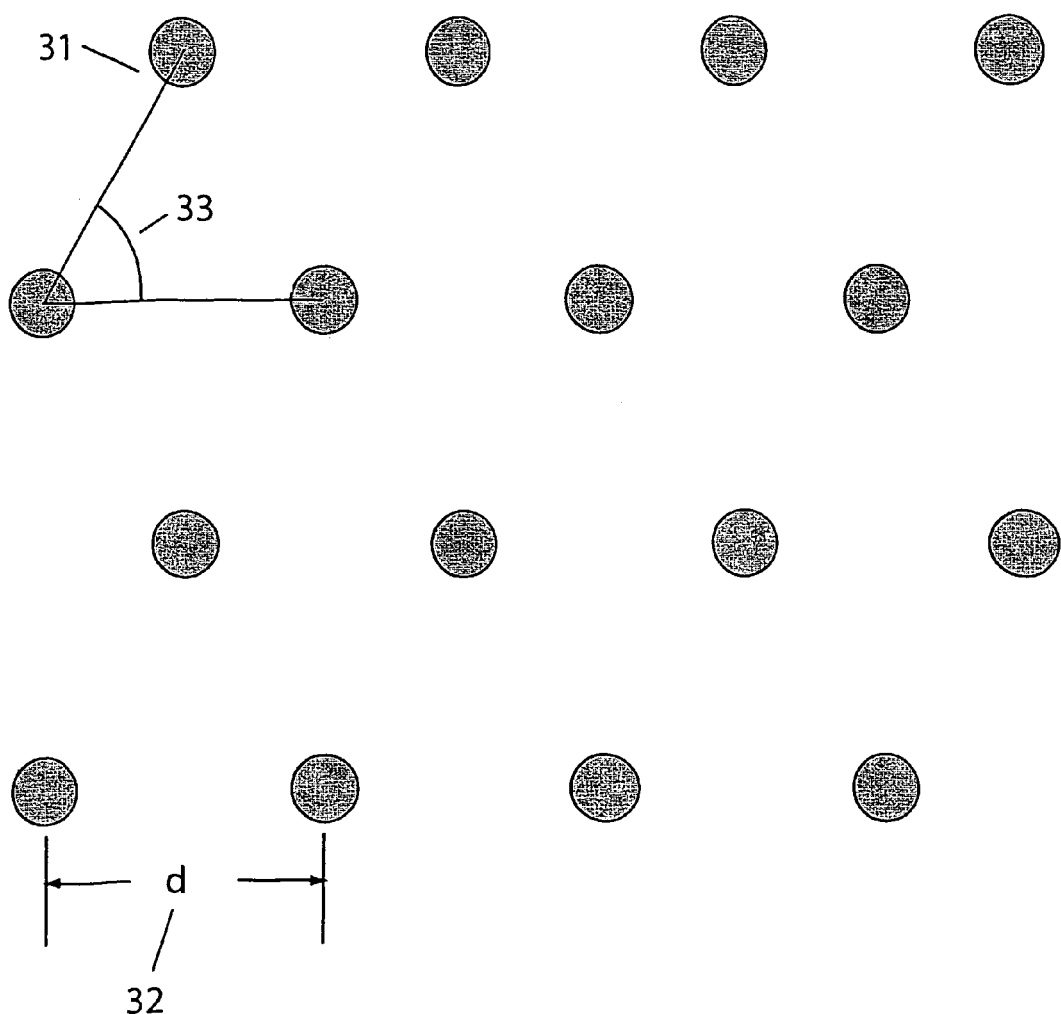
FIG. 2 depicts an array of optical confinement, here zero-mode waveguide, arranged in a non-square format. The annotations of various components shown in the figure are as follows: 31: the ZMW. 32: the distance between adjacent ZMWs. 33: the angle formed between the any three adjacent ZMWs (60 degrees).
Figure 3:
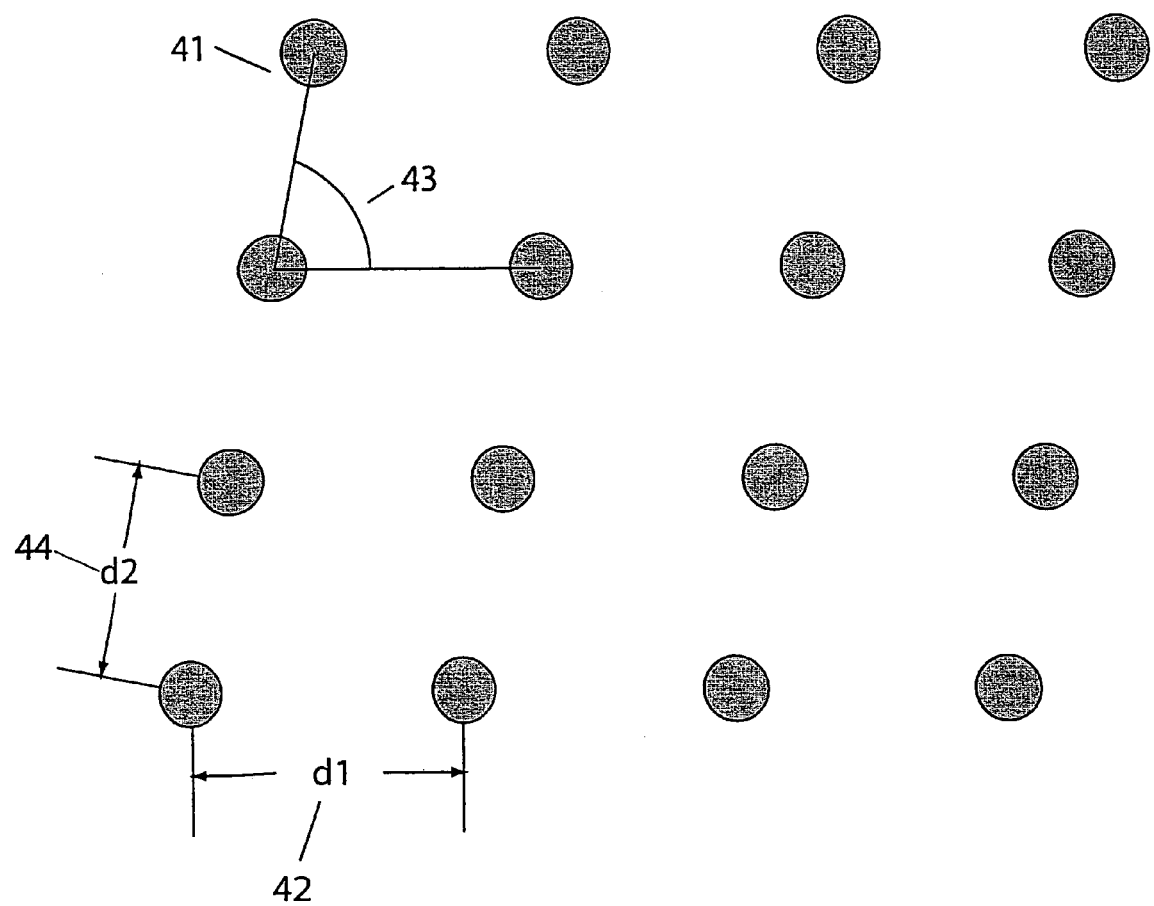
FIG. 3 depicts an illustrative 2-dimentional array with an illustrative angle and two different unit vector lengths. The annotations of various components shown in the figure are as follows: 41: ZMW. 42: first distance d1. 43: unit vector angle. 44: second distance.
Figure 4:
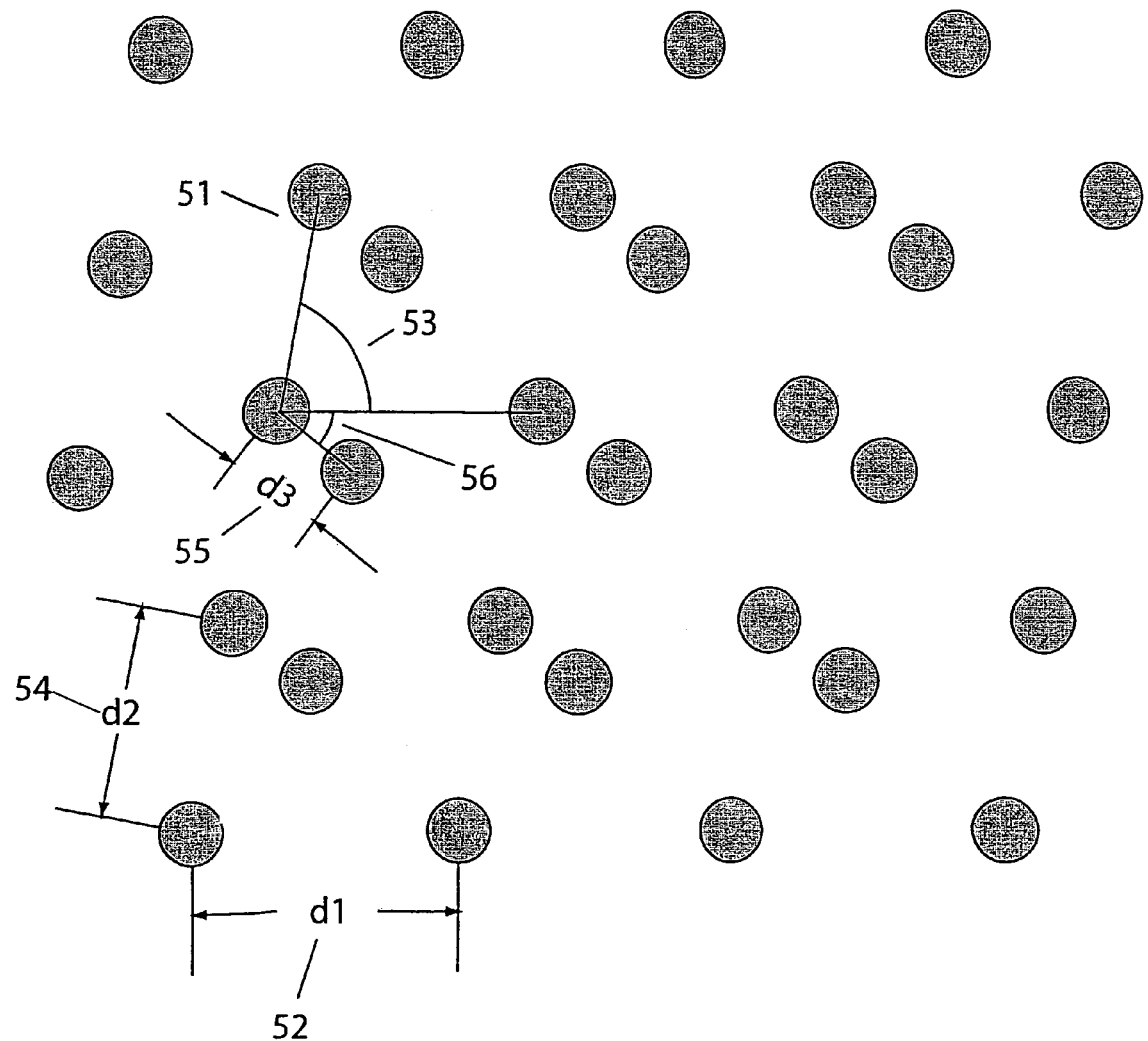
FIG. 4 depicts an illustrative regular disposition of ZMWs. In this configuration, there is a lattice defined by the parameters d1, d2 and the angle 53. In addition to a ZMW at each lattice point, there is a complex unit cell that comprises a plurality of ZMWs in an arrangement that is defined by a list of angles and distances with one angle and one distance for each element of the unit cell. While this figure shows an array with a unit cell of two components, the unit cell can have any number of elements. The annotations of various components shown in the figure are as follows: 51: ZMW. 52: first lattice distance. 53: lattice angle. 54: second lattice distance. 55: unit cell first distance. 56: unit cell first angle.
Figure 5:
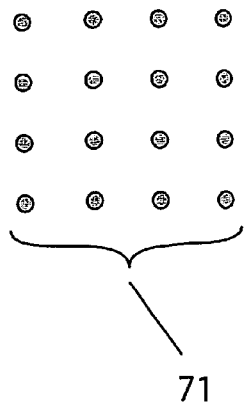
FIG. 5 depicts an array of arrays. The annotations of various components shown in the figure are as follows: 71: an array of zero mode waveguides. 72: a super array of elements of which the array 71 is a portion thereof.
Figure 5:
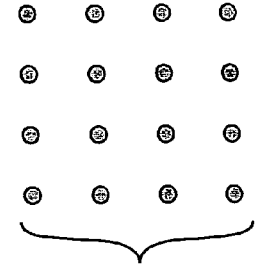
Figure 5:
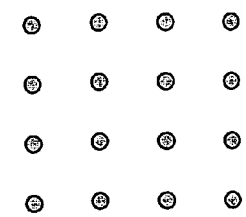
Figure 5:
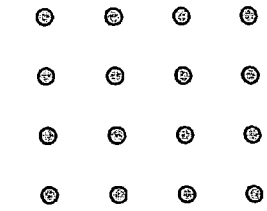

General Techniques:

The practice of the present invention will employ, unless otherwise indicated, conventional techniques of Integrated Circuit (IC) processing biochemistry, chemistry, molecular biology, genomics and recombinant DNA, which are within the skill of the art. See, e.g., Stanley Wolf et al., SILICON PROCESSING FOR THE VLSI ERA, Vols 1–4 (Lattice Press); Michael Quirk et al., SEMICONDUCTOR MANUFACTURING TECHNOLOGY; Sambrook, Fritsch and Maniatis, MOLECULAR CLONING: A LABORATORY MANUAL, $2^{nd}$ edition (1989); the series METHODS IN ENZYMOLOGY (Academic Press, Inc.): PCR 2: A PRACTICAL APPROACH (M. J. MacPherson, B. D. Hames and G. R. Taylor eds. (1995).

Definitions:

As used in the specification and claims, the singular form "a", "an" and "the" include plural references unless the context clearly dictates otherwise.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" or "luminescent signal" may have any one of the above-described properties.

The term "electromagnetic radiation" refers to electromagnetic waves of energy including, in an ascending order of frequency (or alternatively, in a descending order of wavelength), infrared radiation, visible light, ultraviolet (UV) light, X-rays, and gamma rays.

A "primer" is a short polynucleotide, generally with a free 3'—OH group, that binds to a target nucleic acid (or template) potentially present in a sample of interest by hybridizing with the target nucleic acid, and thereafter promoting polymerization of a polynucleotide complementary to the target.

The terms "operatively linked to" or "operatively coupled to" are used interchangeably herein. They refer to a juxtaposition wherein the components so described are in a relationship permitting them to function in their intended manner.

Structure of the Optical Confinements of the Present Invention

One central aspect of the present invention is the design of optical devices and methods for characterizing molecules and/or monitoring chemical reactions. Distinguished from the previously reported nanostructures, the optical devices of the present invention allow multiplexing a massive quantity of single-molecule analysis under physiologically relevant conditions.

In one embodiment, the present invention provides a high density array of optical confinements having a surface density exceeding $4 \times 10^4$ confinements per $mm^2$, wherein the individual confinement in the array provides an effective observation volume on the order of zeptoliters. Preferably, the individual confinement in the array provides an effective observation volume less than about 1000 zeptoliters, more preferably less than about 900, more preferably less than about 80, even more preferably less than about 10 zeptoliters. Where desired, an effective observation volume less than 1 zeptoliter can be provided. In a preferred aspect, the individual confinement yields an effective observation volume that permits resolution of individual molecules present at a physiologically relevant concentration. The physiologically relevant concentrations for most biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu M$), or more preferably higher than 50 $\mu M$, or even higher than 100 $\mu M$.

To achieve the required observation volume for single-molecule analyses under physiologically relevant conditions, the subject array generally comprises zero-mode waveguide or alternative nanoscale optical structures. Such alternative structures include but are not limited to porous films with reflective index media, and confinement using index matching solids.

As used herein, "zero-mode waveguide" refers to an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation. Suitable materials for fabricating the cladding include but are not limited to alloys, metals, and semi-conducting materials, and any combination thereof. Alloys include any of the numerous substances having metallic properties but comprising two or more elements of which at least one is a metal. Alloys may vary in the content or the amount of the respective elements-whether metallic or non metallic. Preferred alloys generally improve some desirable characteristics of the material over a pure elemental material. Characteristics that can be improved through the use of mixtures of materials include, chemical resistance, thermal conductivity, electrical conductivity, reflectivity, grain size, coefficient of thermal expansion, brittleness, temperature tolerance, conductivity, and/or reduce grain size of the cladding.

In general, alloys suitable for the present invention may involve mixtures where one component is present at fractions as low as 0.0001%. In other instances, alloys with large fractions of more than one compound will be desirable. One embodiment of the ZMW uses aluminum as the cladding of the ZMW structure. As an example of how alloys can be beneficial to a ZMW structure, it is useful to consider different alloys of aluminum in how they would affect a ZMW. In the art of Metalurgy, numerous materials are alloyed with aluminum. Non-limiting examples of materials suitable to alloy with aluminum are antimony, arsenic, beryllium, bismuth, boron, cadmium, calcium, carbon, cerium, chromium, cobalt, copper, gallium, hydrogen, indium, iron, lead, lithium, magnesium, manganese, mercury, molybdenum, nickel, niobium, phosphorous, silicon, vanadium, zinc and others. By way of example of how the introduction of another element could beneficially impact the ZMW performance, the introduction of boron to aluminum is known in the art of metallurgy to increase the conductivity of aluminum. An increase in conductivity of the metal film could improve the performance by decreasing the penetration depth thereby decreasing the observation volume. A preferred embodiment includes an alloy of aluminum that is more than 0.0001% of a dopant. A more preferred embodiment includes an alloy of aluminum that is more than 0.005% of a dopant. A still more preferred embodiment includes an allow of aluminum that is more than 0.1% of a dopant.

In contrast, some materials are expected to decrease the performance of the ZMW structure, and in these instances it will be desirable to take measures to eliminate certain impurities. For example, in certain applications it may be desirable to decrease the amount of lead or arsenic if toxicity of the device is a concern. A preferred embodiment of the device includes a metal film that is less than 1% arsenic. A more preferred embodiment of the device includes a metal films that is less than 0.1% arsenic. A still more preferred embodiment includes a metal film that is less than 0.001% arsenic. A still more preferred embodiment includes a metal film that is less than 0.00001% arsenic. An additional preferred embodiment includes a metal film that is less than 1% lead. A still more preferred embodiment includes a metal film that is less than 0.1% lead. A still more preferred embodiment includes a metal film that is less than 0.01% lead. A still more preferred embodiment includes a metal film that is less than 0.001% lead. A still more preferred embodiment includes a film that is less than 0.00001% lead. In other applications where optical confinement performance is especially important, impurities that tend to reduce the conductivity, thereby worsening the confinement, will be undesirable. For example, vanadium is known in the art of metallurgy to reduce the conductivity of aluminum. A preferred embodiment includes a metal film that is less than 0.1% vanadium. A still more preferred embodiment includes a metal film that is less than 0.01% vanadium. A still more preferred embodiment includes a film that is less than 0.001% vanadium.

Semi-conducting materials suitable for fabricating the cladding are generally opaque, and they include silicon, silicates, silicon nitride, silicon dioxide, gallium phosphide, gallium arsenide, or any combinations thereof.

The cladding of the subject zero-mode waveguide may be coated with materials to improve the surface quality. For instance, coating may enhance the durability of the cladding material. In addition, coating is particularly desirable if the reactants contained in the core are prone to interact or adhere to the cladding material. A variety of appropriate coating materials are available in the art. Some of the materials may covalently adhere to the surface, others may attach to the surface via non-covalent interactions. Non-limiting examples of coating materials include aluminum oxide film, silanization reagent such as dimethychlorosilane, dimethydichlorosilane, hexamethyldisilazane or trimethylchlorosilane, polymaleimide, and siliconizing reagents such as silicon oxide, Aquasil™, and Surfasil™

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda_c$). For a circular guide of diameter d and having a clad of perfect conductor, $\lambda_c$ is approximately 1.7×d. The cross sectional area of the core may be circular, elliptical, oval, conical, rectangular, triangular, polyhedral, or in any other shape. Although uniform cross sectional area is preferred, the cross sectional area may vary at any given depth of the guide if desired.

In a preferred embodiment, the core is non-cylindrical. In one aspect of this embodiment, a non-cylindrical core comprises an opening on the upper surface and a base at the bottom surface that is entirely enclosed by the cladding, wherein the opening is narrower in lateral dimension than the base. This configuration significantly restricts the diffusion of reactants, and hence increases the average residence time in the observation volume. Such configuration is particularly useful for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

The zero-mode waveguides embodied in the present invention have a relatively high fill fraction ratio, typically above 0.0001, preferably above 0.001, more preferably above 0.01, and even more preferably above 0.1. As used herein, "fill fraction" of a pattern refers to the ratio of the area occupied by the foreground of the pattern to the area occupied by the background of the pattern. In the context of zero-mode waveguide, the foreground is considered to be the area occupied by the core of the zero-mode waveguide, and the background is the area between the zero-mode waveguide and the cladding (e.g., the aluminum film that forms the cladding in certain designs). The zero-mode waveguides with high fill fraction ratios are particularly useful for performing homogenous assays. The fill fraction can be calculated by summing the total areas of all of the zero-mode waveguides in the array and dividing by the total available area including both the zero-mode waveguides and the spaces between them. For example, if a zero-mode waveguide has a diameter of 50 nm, then the area of this zero-mode waveguide is 1962.5 nm². If these zero-mode waveguides are in a square array separated by 100 nm, the total available area is 10,000 square nanometers for each zero-mode waveguide. Therefore, the array has a fill fraction which would provide nearly four orders of magnitude higher signal strength in a surface binding assay than a zero-mode waveguide having a fill fraction on the order of 0.01%.

In a bioassay such as an ELISA or other molecular binding bioassay, one limitation is the inability to operate "homogeneously", or in a mode where solutions may be added to a mixture but nothing removed. This complicates highly multiplexed assays, as provisions for both adding and removing material from a large number of wells is significantly more complex than the provisions for simply adding materials. In the case of the ELISA assay, the removal of materials is necessary, because the fluorescent (or other) markers that remain free in solution at the end of the assay would interfere with the ability to detect markers bound to the reaction surface. Techniques to overcome this have been devised to exploit the short range of radioactive emissions from certain radioisotopes, but these techniques have inherent difficulties associated with personnel safety and waste disposal. Other methods for confining the sensitivity of the assay to the surface have been devised, such as total internal reflection confinement (TIR), and confocal detection. The zero-mode waveguide photonic structure allows a simpler and less expensive optical system configuration than either of these techniques, and vastly outperforms both from the perspective of confinement of sensitivity to the surface.

The fill fraction is important in bioassays, because the effective probe area is limited to the surface area of the bottoms of the zero-mode waveguide in the detection region. The amount of signal detectable in such an assay will be directly proportional to the available area, and having a larger fraction of the available surface occupied by zero-mode waveguides will thus increase the signal strength of measurements of such assays. A high fill fraction structure would be generally useful in any surface sensitivity application, not limited to the ELISA assay.

The cutoff wavelength is defined as the wavelength above which the waveguide is essentially incapable of propagating electromagnetic energy along the waveguide under the illumination geometry used. Given the geometry of the core, and the properties of the cladding material, as well as the wavelength of the incident electromagnetic radiation, one skilled in the art can readily derive the cutoff wavelength by solving the Maxwell's equations (see, e.g., John D. Jackson, CLASSICAL ELECTRODYNAMICS, second edition, John Willey and Sons). The choice of the incident wavelength will depend on the particular application in which the subject array is to be employed. In certain aspects, the incident wavelength may be selected from a range of about 10 nm to about 1 mm. For detecting fluorescent signals, the incident wavelength is typically selected from the range of about 380 nm to about 800 nm. Polarized (linearly or preferably circularly polarized) or unpolarized incident radiation is generally employed to illuminate the array in order to create a desired observation volume.

In a separate embodiment, the present invention provides an alternative optical confinement termed external reflection confinement (ERC). In contrast to the conventional total internal reflection confinement (IRC), the low index medium is the electromagnetic radiation carrier, and the high index (and opaque) medium is the reflector. As such, the roles of the refractive indices are reversed as compared to the IRC situation. ERC generally requires some kind of means to provide the analyte (i.e., the molecules under investigation) in the opaque phase.

IRC relies on reflection of an electromagnetic radiation incident on an interface between high index of refraction and low index of refraction. When light is incident above the critical angle of total internal reflection (known in the art), all of the incident electromagnetic radiation is reflected and none is transmitted into the low index phase. A thin region of evanescent radiation is established proximal to the interface on the low index side. This radiation field is typically an exponentially decaying field with an attenuation length in the range from about 100 nm to about 200 nm, depending on the angle of incidence and the indices of refraction of the two phases. If the low index phase is a solution containing an analyte, then the evanescent radiation can be used to probe the analyte in the solution with a high degree of surface sensitivity.

In ERC, the carrier of the propagating electromagnetic radiation is a transparent low index film, and the analyte-bearing medium is a high-index metallic opaque film. In this case, most of the radiation is reflected irrespective of the angle of incidence, and non-reflected light is rapidly attenuated according to the skin depth of the metal. Typically, means is provided to convey the analyte within the metal phase. Theses means can take the form of a nanocapillary tube constructed within the metal layer. When sufficiently small, the presence of such a tube will have little effect on the distribution of energy in the two media, but can be amply large enough to convey biomolecules. To be small enough, any defects in the metal film must be small compared with the wavelength of the illumination. This can be achieved because of the large ratio between the wavelength of visible light, and the typical size of biomolecules of interest. While visible light is typically between 400 nm and 750 nm in wavelength, biomolecules of interest are generally in the vicinity of 1–30 nm in diameter. The attenuation of the radiation at the interface can be used to confine illumination to a very small region of the analyte. A small hole in an index matched (to water) film on a high index substrate could provide lateral confinement beyond what is possible with diffraction limited optics in the TIR context. This could give 100 zeptoliter confinement in principle. In this method, a version of total internal reflection confinement is used in which a solid material index-matched to the analyte solution is applied to the substrate surface and then perforated with nanoscale holes. When used in TIR mode, these structures will provide additional confinements above what can be obtained with TIR alone.

Other alternative confinements are index matching solids. As an illustrative example, such optical confinement can be fabricated starting with a high index transparent susbtrate such as sapphire, spin coat 200 nm of PMMA (polymethyl methacrylate) resist resin. Exposure to electron beam lithography will render isolated spots soluble according to the pattern applied. After development, the device will have nano-scale holes in the PMMA layer and are ready to be used in a TIR setup. Axial confinement is unaffected by the PMMA layer, as it has nearly the same index of refraction as the solution containing the analyte, but the solution is physically prevented from approaching near the surface except where the holes are situated, providing a degree of lateral confinement given by the diameter of the holes.

The subject optical confinements can be provided with an optical system capable of detecting and/or monitoring interactions between reactants at the single-molecule level. Such optical system achieves these functions by first generating and transmitting an incident wavelength to the reactants contained in the confinements, followed by collecting and analyzing the optical signals from the reactants.

The optical system applicable for the present invention comprises at least two elements, namely an excitation source and a photon detector. The excitation source generates and transmits incident light used to optically excite the reactants contained in the optical confinement. Depending on the intended application, the source of the incident light can be a laser, a light-emitting diode (LED), a ultra-violet light bulb, and/or a white light source. Where desired, more than one source can be employed simultaneously. The use of multiple sources is particularly desirable in case of detecting more than one fluorescent signal to track the interactions of more than one or one type of molecules simultaneously. A wide variety of photon detectors are available in the art. Representative detectors include but are not limited to optical reader, high-efficiency photon detection system, photodiode (e.g. avalanche photo diodes (APD)), camera, charge couple device (CCD), electron-multiplying charge-coupled device (EMCCD), intensified charge coupled device (ICCD), and confocal microscope. Where desired, the subject arrays of optical confinements contain various alignment aides or keys to facilitate a proper spatial placement of the optical confinement and the excitation sources, the photon detectors, or the optical transmission element as described below.

The subject optical system may also include an optical transmission element whose function is manifold. First, it collects and/or directs the incident wavelength to the optical confinement containing the reactants. Second, it transmits and/or directs the optical signals emitted from the reactants inside the optical confinement to the photon detector. Third, it may select and/or modify the optical properties of the incident wavelengths or the emitted wavelengths from the reactants. Illustrative examples of such element are diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), waveplates, and delay lines. In some embodiments, the optical transmission element can be planar waveguides in optical communication with the arrayed optical confinements. For instance, a planar waveguides can be operatively coupled to an array of zero-mode waveguides to directly channel incident wavelengths to the respective cores of the zero-mode waveguides so as to minimize the loss of wave energy. The planar channel can be included as a detachable unit located at the base of array substrate, or it can be bonded to the substrate as an integral part of the array.

The optical transmission element suitable for use in the present invention encompasses a variety of optical devices that channel light from one location to another. Non-limiting examples of such optical transmission devices include optical fibers, diffraction gratings, arrayed waveguide gratings (AWG), optical switches, mirrors, lenses (including microlens and nanolens), collimators, and any other devices that guide the transmission of light through proper refractive indices and geometries.

In a preferred embodiment, the optical confinement of the present invention is operatively coupled to a photon detector. For instance, the arrayed optical confinement is operatively coupled to a respective and separate photon detector. The confinement and the respective detector can be spatially aligned (e.g., 1:1 mapping) to permit an efficient collection of optical signals from the waveguide. A particularly preferred setup comprises an array of zero-mode waveguides, wherein each of the individual waveguides is operatively coupled to a respective microlens or a nanolens, preferably spatially aligned to optimize the signal collection efficiency.

The subject arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

As described above, the subject arrays comprise a plurality of optical confinements. In some embodiments, the arrays have at least about $20 \times 10^4$ distinct optical confinements, preferably at least about $20 \times 10^6$ distinct confinements, and more preferably at least about $20 \times 10^8$ confinements. The density of the spots on the solid surface in certain embodiments is at least above $4 \times 10^4$ confinements per $mm^2$, and usually at least about $8 \times 10^4$, at least about $1.2 \times 10^5$, or at least about $4 \times 10^6$ confinements per $mm^2$, but does not exceed $4 \times 10^{12}$ confinements per $mm^2$, and usually does not exceed about $4 \times 10^{10}$ confinements per $mm^2$. The overall size of the array generally ranges from a few nanometers to a few millimeters in thickness, and from a few millimeters to 50 centimeters in width or length. Preferred arrays have an overall size of about few hundred microns in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements should be placed close to each other relative to the incident wavelength.

Accordingly, the present invention provides array of zero-mode waveguides comprising at least a first and at least a second zero-mode waveguide, wherein the first zero-mode waveguide is separated from the second zero-mode waveguide by a distance such that upon illumination with an incident wavelength, intensity of diffractive scattering observed from the first zero-mode waveguide at a given angle is less than that if the first zero-mode waveguide were illuminated with the same incident wavelength in the absence of the second zero-mode waveguide. A reduced intensity of diffractive scattering is observed when the first and the second confinements are placed at the diffraction limit. Diffractive scattering can be reduced or significantly eliminated if an array comprises zero-mode waveguides spaced in a regular spaced lattice where the separation of zero-mode waveguide s from their nearest neighbors is less than half the wavelength of the incident wavelength. In this regime, the structure behaves as a zero-order grating. Such gratings are incapable of scattering incident light despite having a large number of elements that by themselves would scatter very effectively. This arrangement is highly desirable for illumination approaches such as dark field illumination, where surface scattering would cause excitation radiation to be collected by the objective lens, thus increasing background noise. Useful wavelengths for illumination range from 250 nm up to 8 microns, meaning that an array of zero-mode waveguides with a spacing of less than 4000 nm would still be useful for application in this manner. A spacing of less than 2000 nm is more preferable, while a spacing of less than 1000 nm is even more preferable in this respect. Some configurations with spacing larger than one half of the wavelength can have the same advantage if the illumination is applied asymmetrically, or if the collection cone angle is configured to be less than 90 degrees. In addition to the benefit of reduced diffractive scattering, narrow spacing between the individual confinements decreases the illumination area and thus lowers the power demand.

Arrays having the optical confinements spaced far apart relative to the incident wavelength also have desirable properties. While the angle-dependent scattering raises the background signal that could be disadvantageous for certain applications, it provides a means particularly suited for characterizing the size and shape of the optical confinements. It also readily permits ensemble bulk measurements of molecule interactions, involving especially unlabelled molecules. Arrays suited for such applications generally contain individual confinements separated by more than one wavelength of the incident radiation, usually more than 1.5 times the incident wavelength, but usually does not exceed 150 times the incident wavelength.

Kits of the Present Invention

The present invention also encompasses kits containing the optical confinement arrays of this invention. Kits embodied by this invention include those that allow characterizing molecules and/or monitoring chemical reactions at a single-molecule level. Each kit necessarily comprises the devices and reagents which render such characterization and/or monitoring procedure possible. Depending on the intended use of the kit, the contents and packaging of the kit will differ. Where the kit is for DNA sequencing, the kit typically comprises: (a) an array of optical confinements, preferably zero-mode waveguides of the present invention that permits resolution of individual molecules present at a concentration higher than about 1 micromolar; (b) sequencing reagents typically including polymerases, aqueous buffers, salts, primers, and nucleoside triphosphates. Where desired, control nucleic acid of known sequences can be included.

The reagent can be supplied in a solid form or dissolved/suspended in a liquid buffer suitable for inventory storage, and later for exchange or addition into the reaction medium when the test is performed. Suitable individual packaging is normally provided. The kit can optionally provide additional components that are useful in the procedure. These optional components include, but are not limited to, buffers, capture reagents, developing reagents, labels, reacting surfaces, control samples, instructions, and interpretive information. Diagnostic or prognostic procedures using the kits of this invention can be performed by clinical laboratories, experimental laboratories, practitioners, or private individuals.

Preparation of the Subject Optical Confinements

The array of the present invention can be manufactured using nanofabrication techniques provided by the present invention, as well as those known in the fields of Integrated Circuit (IC) and Micro-Electro-Mechanical System (MEMS). The fabrication process typically proceeds with selecting an array substrate, followed by using appropriate IC processing methods and/or MEMS micromachining techniques to construct and integrate the optical confinement and other associated components.

Array Substrate:

In some embodiments, the array of optical confinements is present on a rigid substrate. In other embodiments concerning, e.g., porous films with reflective index media, flexible materials can be employed.

By rigid is meant that the support is solid and does not readily bend, i.e., the support is not flexible. Examples of solid materials which are not rigid supports with respect to the present invention include membranes, flexible metal or plastic films, and the like. As such, the rigid substrates of the subject arrays are sufficient to provide physical support and structure to optical confinements present thereon or therein under the assay conditions in which the array is employed, particularly under high throughput handling conditions.

The substrates upon which the subject patterns of arrays are may take a variety of configurations ranging from simple to complex, depending on the intended use of the array. Thus, the substrate could have an overall slide or plate configuration, such as a rectangular or disc configuration, where an overall rectangular configuration, as found in standard microtiter plates and microscope slides, is preferred. Generally, the thickness of the rigid substrates will be at least about 0.01 mm and may be as great as 1 cm or more, but will usually not exceed about 5 cm. Both the length and the width of rigid substrate will vary depending on the size of the array of optical confinements that are to be fabricated thereon or therein.

The substrates of the subject arrays may be fabricated from a variety of materials. The materials from which the substrate is fabricated is preferably transparent to visible and/or UV light. Suitable materials include glass, semiconductors (e.g., silicate, silicon, silicates, silicon nitride, silicon dioxide, quartz, fused silica, and gallium arsenide), plastics, and other organic polymeric materials.

The substrate of the subject arrays comprise at least one surface on which a pattern of optical confinements is present, where the surface may be smooth or substantially planar, or have irregularities, such as depressions or elevations. The surface on which the pattern of targets is presented may be modified with one or more different layers of compounds that serve to modulate the properties of the surface in a desirable manner. Modification layers of interest include: inorganic and organic layers such as metals, metal oxides, polymers, small organic molecules, functional moieties such as avidin/biotin and the like. The choice of methods for applying the coating materials will depend on the type of coating materials that is used. In general, coating is carried out by directly applying the materials to the zero-mode waveguide followed by washing the excessive unbound coating material. Certain coating materials can be cross-linked to the surface via extensive heating, radiation, and by chemical reactions. Those skilled in the art will know of other suitable means for coating a micro well fabricated on chip, or will be able to ascertain such, without undue experimentation.

Fabrication Process:

Fabrication of the subject chips can be performed according to the methods described as follows or other standard techniques of IC-processing and/or MEMS micromachining. The standard techniques known in the art include but are not limited to electron-beam lithography, photolithography, chemical vapor or physical vapor deposition, dry or wet etching, ion implantation, plasma ashing, bonding, and electroplating. Additional fabrication processes are detailed in the U.S. patent application Publication No. 20030174992, the content of which is incorporated by reference in its entirety.

In a preferred embodiment, the present invention provides a negative tone fabrication process. Unlike the conventional positive tone fabrication process that suffers from the drawback of creating optical confinements of varying dimensions, the subject negative tone process provides far more consistent configurations. A comparison of the two fabrication processes is shown in Table 1 below.

TABLE 1

Positive and Negative Tone Process Steps in Fabrication of Zero-Mode Waveguides

| Step # | Positive Tone Process | Negative Tone Process |
|---|---|---|
| 1 | Clean fused silica substrates in heated solution of hydrogen peroxide and ammonium hydroxide. | Same |
| 2 | Cascade rinse substrates in deionized water. | Same |
| 3 | Clean substrates in oxygen plasma cleaner. | Same |
| 4 | Coat substrates with metal film by either thermal evaporation or sputtering. | Spin-coat substrates with electron-beam resist. |
| 5 | Spin-coat substrates with electron-beam resist over the metal layer. | Bake casting solvent out of film. |
| 6 | Bake casting solvent out of film. | Expose resist with electron beam lithography. |
| 7 | Expose resist with electron beam lithography. | Develop resist in chemical bath to reveal array of small pillars with large empty gaps in resist. |
| 8 | Develop resist in chemical bath to reveal holes. | Rinse developer away and dry chips. |
| 9 | Rinse developer away and dry chips. | Coat chips with metal film by either thermal evaporation or sputtering. |
| 10 | Use reactive-ion etching to transfer resist pattern into metal film. | Dissolving underlying negative resist using Microposit 1165 Stripper. |
| 11 | Strip resist using oxygen plasma. | Same |

In a negative tone process, a negative resist is applied to the substrate. A resist is negative if it is rendered insoluble by application of some agent, where in some cases the agent is optical energy or electron beam energy. Alternatively, a positive tone resist can be used with a negative pattern. A negative tone pattern is characterized by the application of the agent in all areas except the location of the optical confinement, e.g., zero-mode waveguide, contrasted with a positive tone image in which the agent is confined only to the optical confinement area. In either case, after development of the resist, resist remains only in the areas where the optical confinement is intended to lie. It is useful in many cases to use means to achieve an undercut sidewall profile of these remaining resist features. Many techniques exist in the art to obtain undercut sidewalls, for example, in electron beam lithography. For instance, one method is to apply to layers of electron beam resist to the surface sequentially, the upper film having a higher sensitivity to the energy delivered to it by the electron beam. Because the beam has a tendency to spread, a larger area of the upper film will be rendered insoluble than in the lower layer, resulting in an overhang beneath the upper layer as desired.

After development and appropriate cleaning procedures known in the art such as a plasma de-scum procedure, the metal film comprising the optical confinement can be applied by one of several methods, including metal evaporation, molecular beam epitaxy and others. In the case that the resist profile is undercut as discussed above, the metal that is deposited in the regions still occupied by the resist will rest on top of the resist rather than resting on the device surface. The resist layer is subsequently removed by any of several techniques including solvent dissolution either with or without ultrasonication or other mechanical agitation, reactive plasma etching, vaporization or others. The metal which rested on the resist features is removed as the resist is removed ("lifted off"), while the resist resting directly on the substrate remains to form the walls of the optical confinement.

The advantage of this process is that the size of the optical confinement is determined by the size of the resist feature, and does not rely on the fidelity of reactive ion etch pattern transfer mechanisms, which can be highly variable for metal films, especially Aluminum a desirable metal for these devices. The positive tone process is subject to the inherent variation in resist feature sizes plus the variation due to pattern transfer, while the negative tone process is subject to the first variability but not the second. Metal thin film techniques suffer from much less lateral variation, and so the overall accuracy is better. This method also does not rely on the availability of a suitable etch for the metal in question, allowing the application of the process to a much wider selection of metals than the positive tone process.

Figure 6:
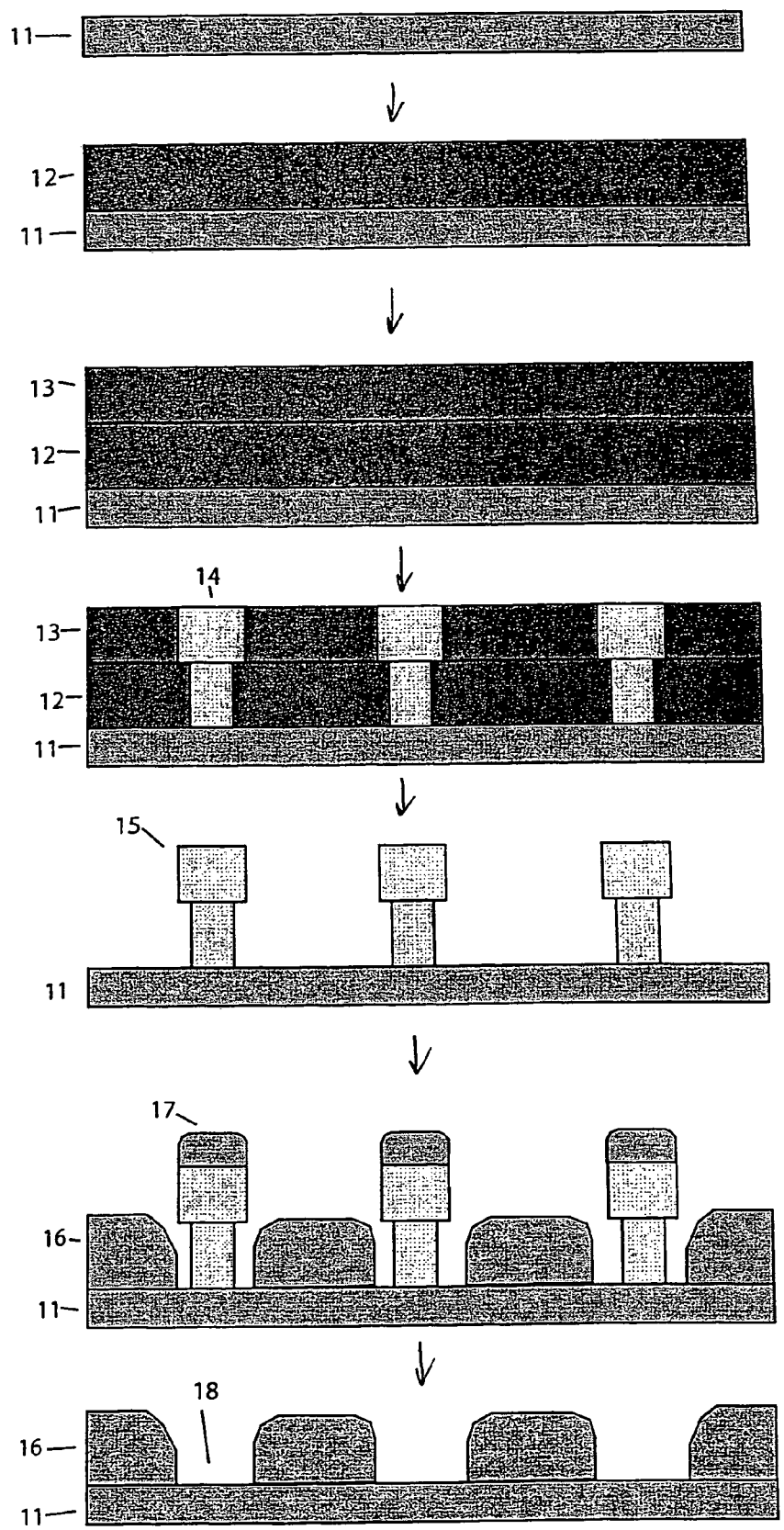
FIG. 6 depicts the process of negative tone fabrication. The annotations of various components shown in the figure are as follows: 11: Substrate. 12: first resist layer. 13: optional second resist layer. 14: latent chemical modification in the film after exposure. 15: resist feature after development. 16: deposited metal film. 17: discontinuous metal cap deposited on resist feature. 18: zero mode waveguide structure.
Figure 7:
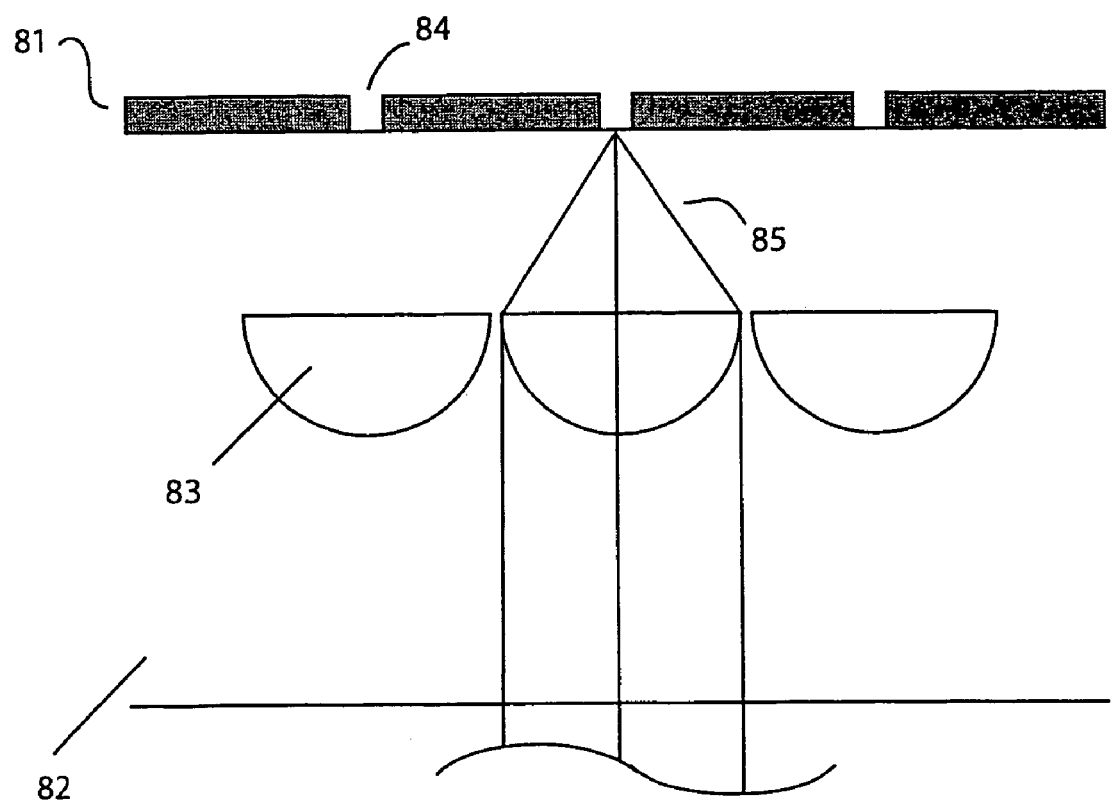
FIG. 7 depicts another illustrative setup. The annotations of various components shown in the figure are as follows: 81: The ZMW film. 82: the glass coverslip. 83: the integral lenses made of a material with a different index of refraction than the glass. 84: the ZMW structure. 85: lines indicating rays of light being focused by the embedded microlens.
Figure 8:
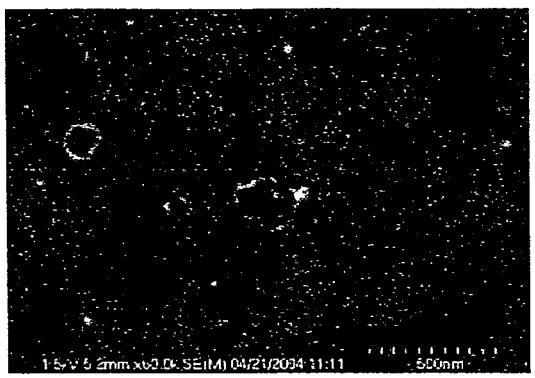
FIG. 8, depicts a scanning electron micrographs of ZMW structures fabricated by positive tone resist (left panels) or negative tone resist (right panels). The grain structure of the polycrystalline film is visible in the image as flecks, and the ZMWs as dark round structures. In contrast to the irregularly shaped structures that are frequently generated by the positive tone process, the negative tone process consistently generates highly regular ZMW configurations.
Figure 8:
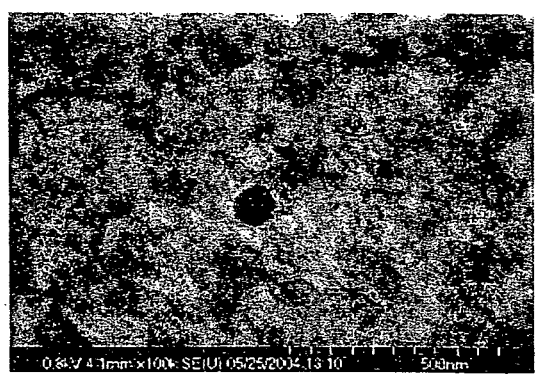
Figure 8:
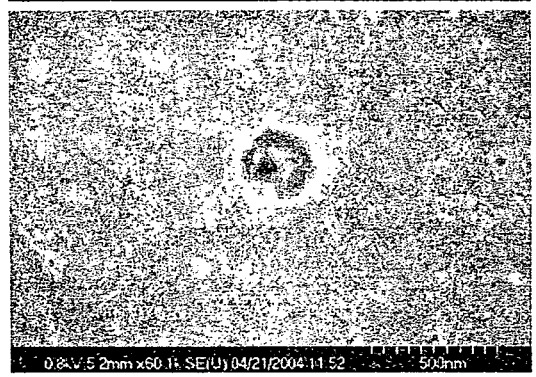
Figure 8:
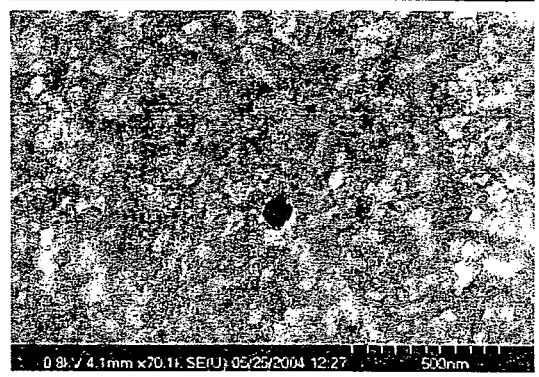

FIG. 6 is a schematic presentation of an illustrative negative tone process to make zero-mode waveguide. In this process, the substrate 11 is first coated with a layer of negative resist 12. Optionally, the substrate can be coated with a second resist layer 13. Exposure of the resist to the same pattern electron beam lithography tool used in the positive tone process, generates the opposite pattern as previously observed, namely one of a periodic array of small pillars of remaining resist, and empty gaps between the pillars 15. The final zero-mode waveguide structures are created by coating this pattern with a thin metal layer such as an aluminum layer 17, and then dissolving the underlying negative resist pillars 18. Because this process is not dependent on the thickness of the alumina layer or the crystal structure or morphology of the metal film, it produces a far more consistent configuration, and provides much finer control over the critical feature size.

A variant negative tone process is termed nanocasting. The steps of nanocasting are similar except that the use of bi-layer resist is avoided. The process first involves depositing on the surface of a substrate (in this case a single-layer resist would be used). The electron beam exposure and development follow, leaving a cylindrical feature for each dot in the exposure pattern. For this process, it is desirable to allow the metal deposition technique to apply material not just on the top of the resist structure but also on the sidewalls of the resist feature. This process is inherently three dimensional, in that a negative replica of the exterior surface of the three-dimensional resist feature is reproduced in the interior surface of the metal films that forms the optical confinement walls. In this case, the undercut resist profile and the various methods used to produce this are not necessary, as in the negative tone process, they are use specifically to prevent contact of the deposited film with the sides of the resist feature. In the nanocasting approach, the deposited film faithfully reproduces the exterior surface of the resist feature, so an undercut figure would only be used if a non cylindrical confinement is desired.

In practicing nanocasting, cautions must be employed to removed the metal from above the nanocasting "master" (the resist feature), as the resist feature can in some instances be entirely buried and unavailable for removal. This, however, can be remedied in a number of ways.

Where the deposition technique has a high degree of anisotropy in the deposition (such as metal evaporation), the sidewalls will be very thin near the top of the resist feature, which in some instances can be a cylindrical pillar. This weak point can be subject to direct mechanical disruption allowing the removal of the metal above the resist feature and hence the ZMW location. An isotropic etch, either solution phase or plasma can be used to further thin the film until this weak point separates, achieving the same effect. If the metal deposition step has a low degree of anisotropy (such as sputtering or electroplating), then the resist material can be exposed through chemical mechanical polishing, or ion milling.

Simultaneous with or subsequent to the removal of the metal cap over the resist feature, the resist material is then removed by solvent dissolution, or reactive ion etching. This completes the fabrication steps, provided the appropriate pattern is applied and the other parameters are correctly chosen.

Uses of the Subject Optical Confinements and other Devices of the Present Invention The subject devices including optical confinements and associated optical systems provide an effective means for analyzing molecules and real-time monitoring chemical reactions.

In certain aspects, the subject devices and methods provide unprecedented performance in single-molecule observation. First, it provides information on individual molecules whose properties are hidden in the statistical mean that is recorded by ordinary ensemble measurement techniques. In addition, because it can be multiplexed, it is conducive to high-throughput implementation, requires smaller amounts of reagent(s), and takes advantage of the high bandwidth of modern avalanche photodiodes for extremely rapid data collection. Moreover, because single-molecule counting automatically generates a degree of immunity to illumination and light collection fluctuations, single-molecule analysis can provide greater accuracy in measuring quantities of material than bulk fluorescence or light-scattering techniques. As such, the subject device and detection/monitoring methods may be used in a wide variety of circumstances including sequencing individual human genomes as part of preventive medicine, rapid hypothesis testing for genotype-phenotype associations, in vitro and in situ gene-expression profiling at all stages in the development of a multi-cellular organism, determining comprehensive mutation sets for individual clones and profiling in various diseases or disease stages. Other applications involve profiling of cell receptor diversity, identifying known and new pathogens, exploring diversity towards agricultural, environmental and therapeutic goals.

In a preferred aspect, the subject devices including various forms of optical confinements and the associated optical systems are particularly suited for conducting single-molecule DNA sequencing. Procedures for conducting single-molecule sequencing are fully described in U.S. Ser. No. 09/572,530, the content of which is incorporated by reference in its entirety.

EXAMPLE 1

The following provides an illustrative process of fabricating zero-mode waveguide. The parameters described herein are meant to be illustrative and not intended to be limiting in any manner.

1. Substrates: Substrates are double polished, 60/40 scratch/dig surface quality, Fused Silica wafers, cut to 100 millimeters(+/−0.2 mm) diameter, and 175 micrometer(+/−25 micrometers) thick and a total thickness variation of less than 25 micrometers.
2. Clean: A mix of 5 parts deionized water, 1 part of (30% v/v Hydrogen Peroxide in water), 1 part of (30% v/v Ammonium Hydroxide in water) is heated to 75 degree Celsius on a hotplate. The wafers are immersed in the mix using a Teflon holder for a duration of 15 minutes.
3. Rinsing: The holder containing the wafers is removed from the RCA clean bath and immersed in a bath of deionized water. The wafers are left in this second bath for a 2 minutes period. The holder still containing the wafers is removed from the bath, and sprayed with deionized water to thoroughly finish the rinsing process.
4. Drying: Within a minute of the final rinsing step, the wafers are dried, while still in the holder, using a dry clean nitrogen flow.
5. Oxygen Plasma: The wafers are then placed in a Glenn 1000 p plasma Asher, used in plasma etch mode (wafers on a powered shelf, and under another powered shelf), with 140 mTorr pressure and 400 Watts of forward power at 40 kHz frequency. The plasma is maintained for 10 minutes. A flow of 18 sccm of molecular oxygen is used.
6. Vapor Priming: The wafers are loaded within 3 minutes after the Oxygen plasma in a Yield Engineering Systems vapor priming oven where they are coated with a layer of HexaMethylDiSilazane (HMDS) adhesion promoter.
7. Electron beam resist coating: The wafers are coated within 15 minutes after the Vapor Priming in a manual spinner unit using NEB-31 electron beam resist (Sumitomo Chemical America). About 3 ml are dispensed on the wafer, which is then spun at 4500 rpm for 60 seconds. Initial acceleration and deceleration are set to 3 seconds 8. Resist Bake: The wafers are baked on a CEE hotplate at a temperature of 115 degree Celsius for 2 minutes. The plate is equiped with a vacuum mechanism that allows good thermal contact between the wafers and the hotplate surface.
9. Gold Evaporation: a layer of 10 nm of gold is then thermally evaporated on the Wafers, on the side coated with the resist. A pressure of less than 2 10e–06 Torr must be reached before the evaporation. The evaporation is performed at a rate of approximately 2.5 Angstrom per second and monitored using an Inficon controller.
10. Electron beam exposure: a pattern consisting of Zero Mode Waveguides is exposed on the wafers, using a high resolution electron beam lithography tool such as a Leica VB6-HR system. Zero mode waveguides are patterned as single exel features. At a current of nominally 1 nano-Ampere, and a Variable Resolution Unit of 1, and for an exel setting of 5 nanometers, doses can range from 10000 microCoulombs per square centimeters to 300000 microCoulombs per square centimeters are used.
11. Gold Etch: After removal from the electron beam system, the 10 nanometer gold layer is removed using gold etchant TFA at room temperature (GE 8148, Transene Corporation), for 10 seconds. Wafers are held in a Teflon holder similar to the one used in step 2.
12. Rinsing: The holder containing the wafers is removed from the gold etchant bath and immerse in a bath of deionized water. The wafers are left in this second bath for a 2 minutes period with gentle manual agitation. The holder still containing the wafers is removed from the bath, and sprayed with deionized water to thoroughly finish the rinsing process.
13. Drying: Within a minute of the final rinsing step, the wafers are dried, while still in the holder, using dry clean nitrogen flow.
14. Post Exposure Bake: The wafers are then submitted to a 2 minute post exposure bake on a hotplate at 95 degree Celsius, equally equipped with a vacuum mechanism.
15. Developing: The wafers are loaded in a Teflon holder and immersed in developer MF-321 (Shipley Chemicals, Rohm-Haas) at room temperature for duration of 30 seconds. Wafers are held in a Teflon holder similar to the one used in step 2.
16. Rinsing: The holder containing the wafers is removed from the developer etchant bath and immerse in a bath of deionized water. The wafers are left in this second bath for a 2 minutes period with gentle manual agitation. The holder still containing the wafers is removed from the bath, and sprayed with deionized water to thoroughly finish the rinsing process.
17. Drying: Within a minute of the final rinsing step, the wafers are dried, while still in the holder, using dry clean nitrogen flow.
18. Surface Descum: The wafers are loaded in a Glenn 1000 p plasma asher run in ashing mode (Wafers on a grounded plate below a powered plate), and submitted to a 30 seconds surface descuming oxygen plasma at a pressure of 140 mTorr and a power of 100 Watts forward power at 40 kHz. A flow of 18 sccm of molecular oxygen is used.
19. Aluminium Evaporation: The wafers are loading in a metal evaporator within 5 minutes of the surface descum process. A layer of 100 nm of thermally evaporated Aluminium is now deposited on the wafers. Evaporation is made at a pressure of no less than 2 10^–6 Torr at a rate of 25 Angstrom per seconds and monitored using an Inficon controller.
20. Aluminium Thickenss measurement: The thickness of the aluminium is measured using a P-10 Profilometer (Tencor).
21. Zero Mode Waveguide Decasting: The Zero Mode Waveguide are decasted from the enclosing Aluminium film by immersing them, in a Teflon holder, in a bath of 1165 Stripper (Shipley Chemicals, Rohm-Haas), or in a bath of AZ-300T Stripper (Shipley Chemicals, Rohm-Haas). The bath is submitted to sonication by immersing the Container holding both the Stripper and the wafer holder in a sonicator. The wafers are left in the decasting bath for 30 minutes
22. Rinsing: The stripping bath is removed from the sonicator. The holder containing the wafers is removed from the stripper bath and immerse in a bath of deionized water. The wafers are left in this second bath for a 2 minutes period with gentle manual agitation. The holder still containing the wafers is removed from the bath, and sprayed with deionized water to thoroughly finish the rinsing process.
23. Drying: Within a minute of the final rinsing step, the wafers are dried, while still in the holder, using dry clean nitrogen flow
24. Photoresist coating: The wafers are coated with Shipley 1827 photoresist spun at a speed of 1500 rpm. About 5 ml of resist is dispensed. Acceleration and deceleration is set to 5 seconds.
25. Resist Bake: The wafers are baked on a CEE hotplate at a temperature of 115 degree Celsius for 15 minutes. The plate is equipped with a vacuum mechanism that allows good thermal contact between the wafers and the hotplate surface.
26. Dicing: The wafer are diced using a K&S-7100 dicing saw (Kulicke & Soffa) using a resin/diamond blade (ADT 00777-1030-010-QIP 600).

The wafers are mounted on a low-tack adhesive tape prior to dicing.

27. Die Removal: The dies are removed from the adhesive tape manually and stored.
28. Resist removal: The layer of 1827 photoresist is removed by immersing the dies first in an acetone bath for 1 minute, then in a 2-propanol bath for 2 minute with gentle manual agitation.
29. Die Drying: The die is dried after being removed from the 2-propanol bath using dry clean air.
30. Plasma Clean: The wafers are loaded in a Drytek 100 plasma etcher, and submitted to a 1 minute oxygen plasma at a pressure of 140 mTorr, a molecular oxygen flow of 85 sccm oxygen and an RF power of 500 Watts forward power at 13 Mhz.

EXAMPLE 2

Figure 9:
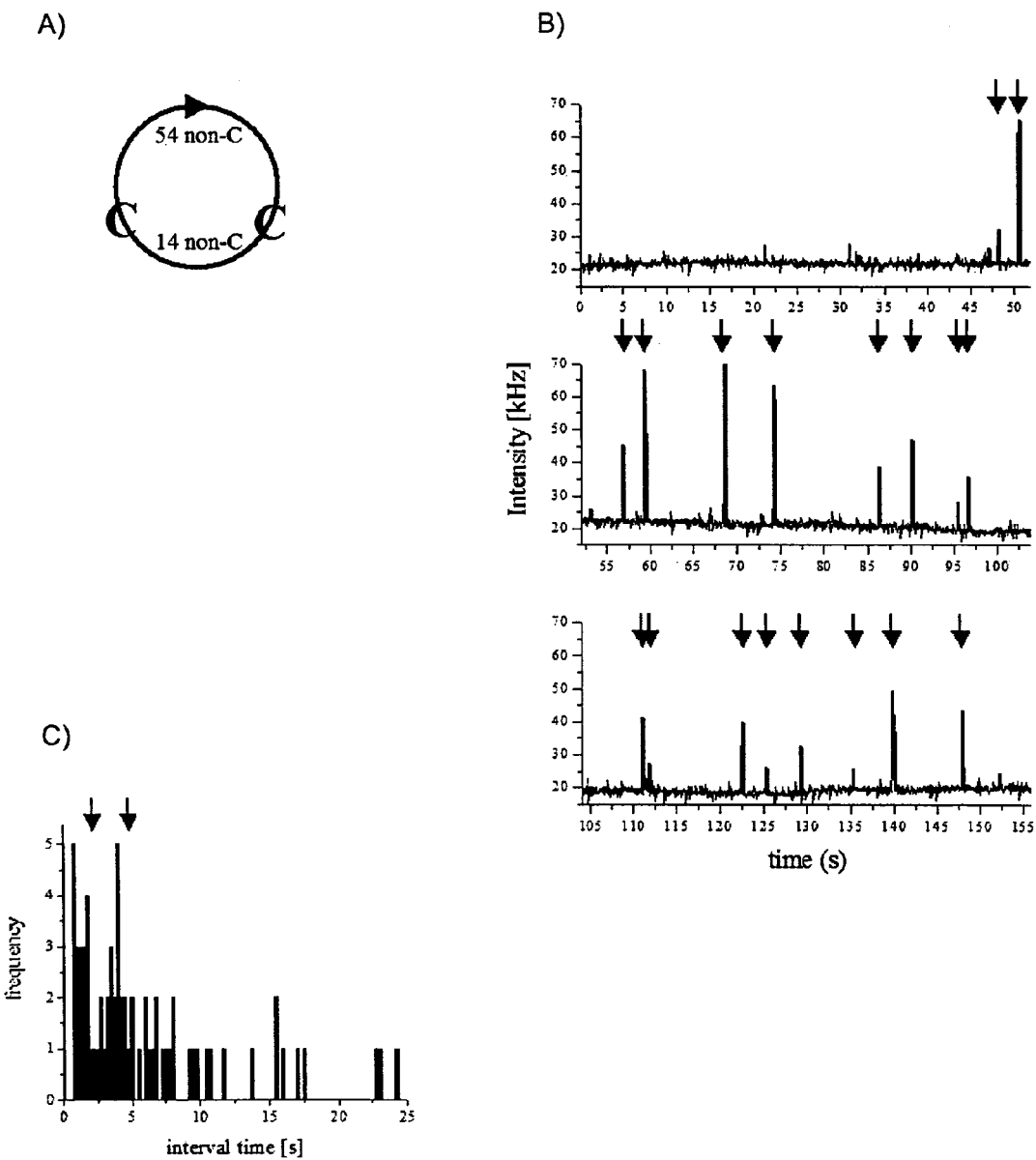
FIG. 9, depicts a single-molecule DNA sequence pattern recognition in ZMWs using artificial pre-formed replication forks. (A) Schematics of the strand to be synthesized of the preformed fork used here. Only two, asymmetrically spaced R110-dCTPs are to be incorporated in this template. (B) Fluorescence time trace of DNA synthesis from a single DNA polymerase in a ZMW. (C) Histogram of burst intervals from the full time trace, a section of which is shown in (B).
Figure 10:
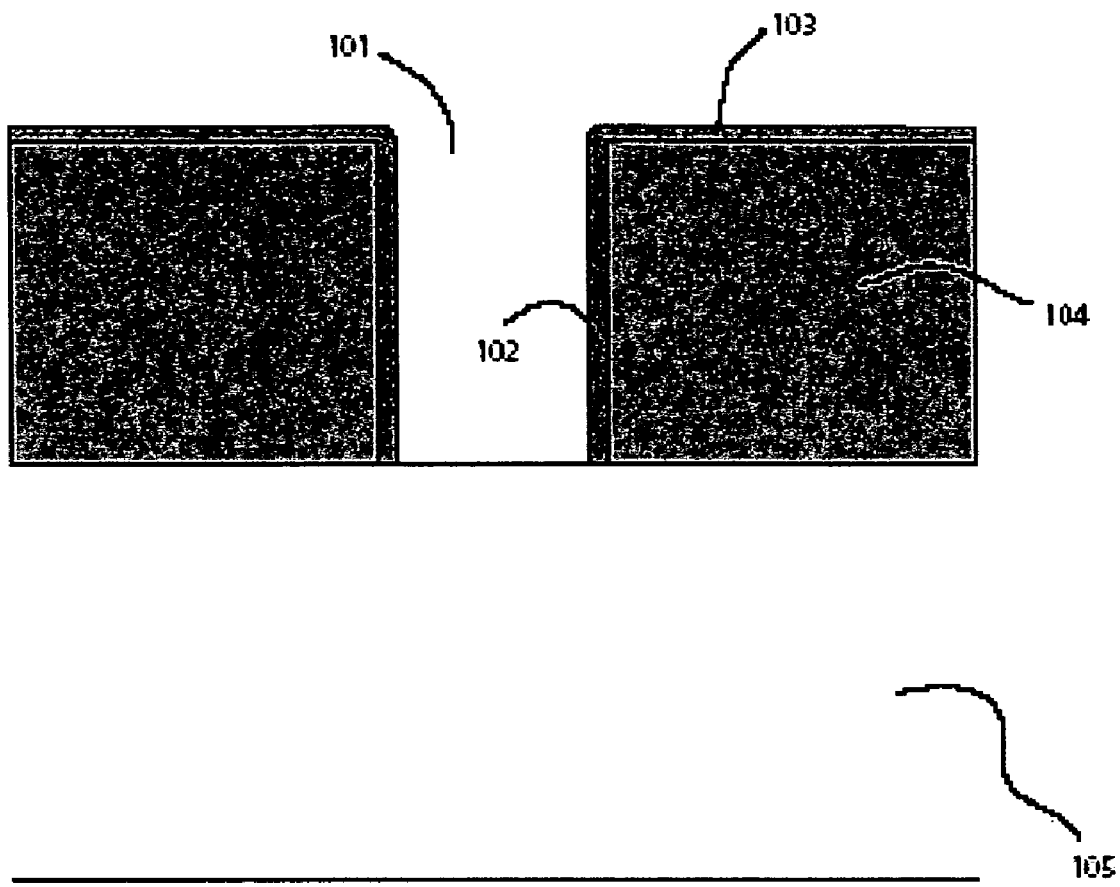
FIG. 10, depicts an illustrative ZMW coated with a thin film. The annotations of various components shown in the figure are as follows: 101: the ZMW. 102: Side walls inside the ZMW. 103: coating on the upper surface of the ZMW. 104: metal film. 105: substrate.
Figure 11:
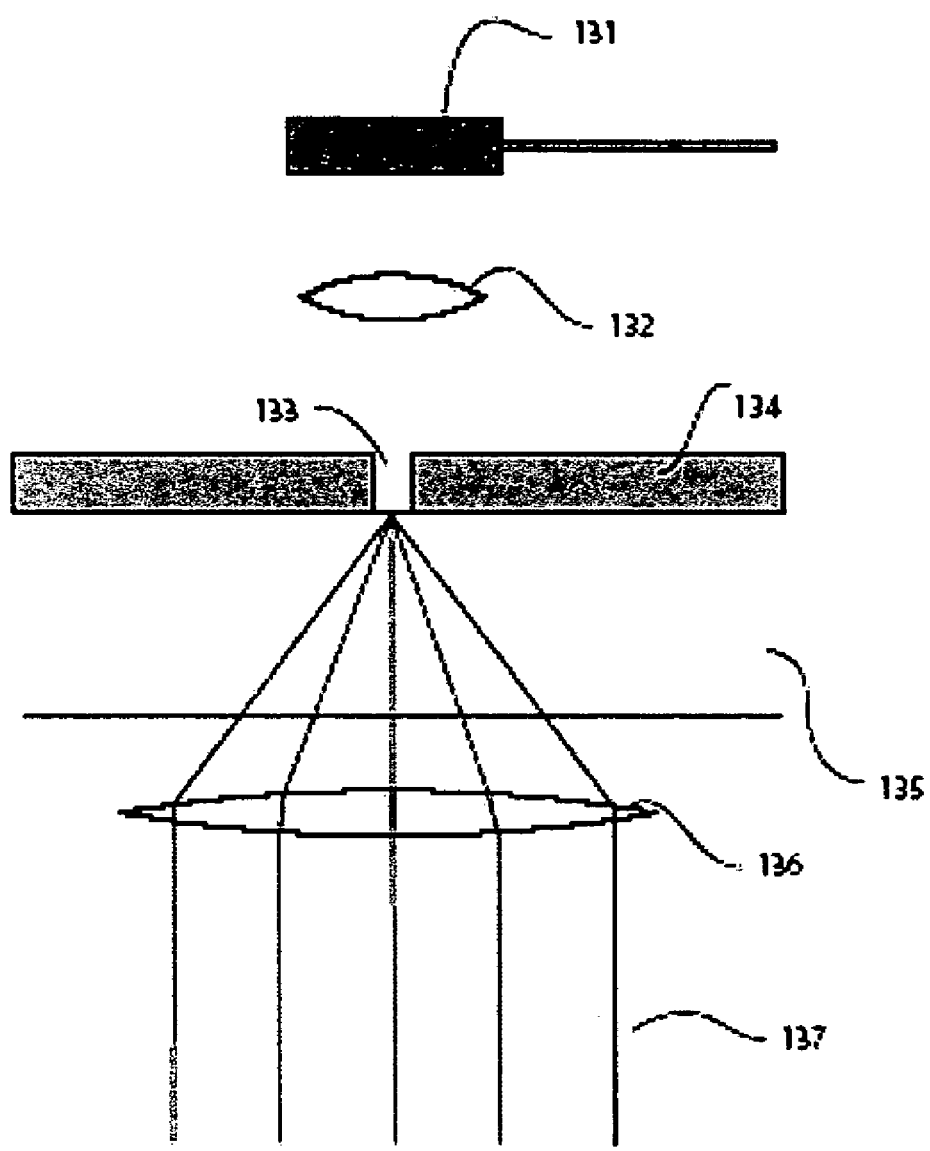
FIG. 11 depicts one alignment strategy. The annotations of various components shown in the figure are as follows: 131: photodetector. 132: optional lens for collecting light. 133: ZMW. 134: metal film. 135: Substrate. 136: objective lens to be aligned. 137: example rays passing through objective to ZMW.
Figure 12:
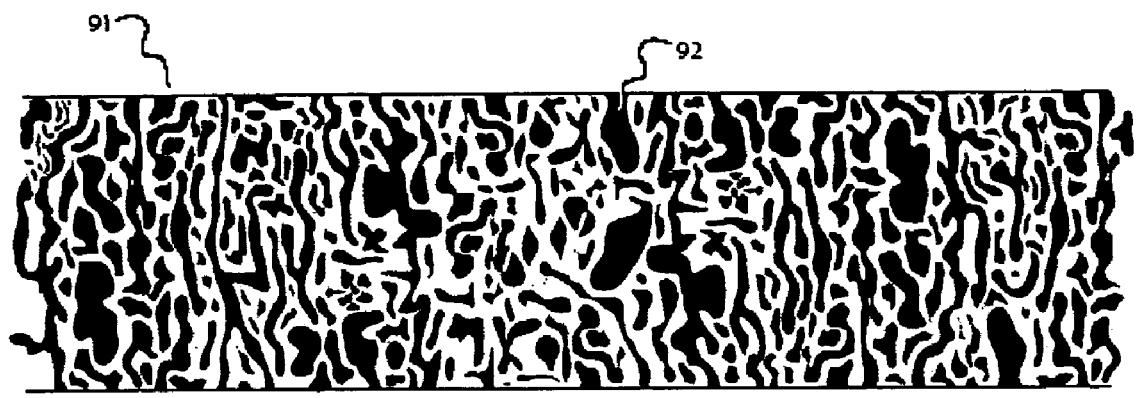
FIG. 12 depicts an alternative optical confinement made of porous film on a substrate. The annotations of various components shown in the figure are as follows: 91: porous film. 92: pore in porous film. 93: substrate.
Figure 13:
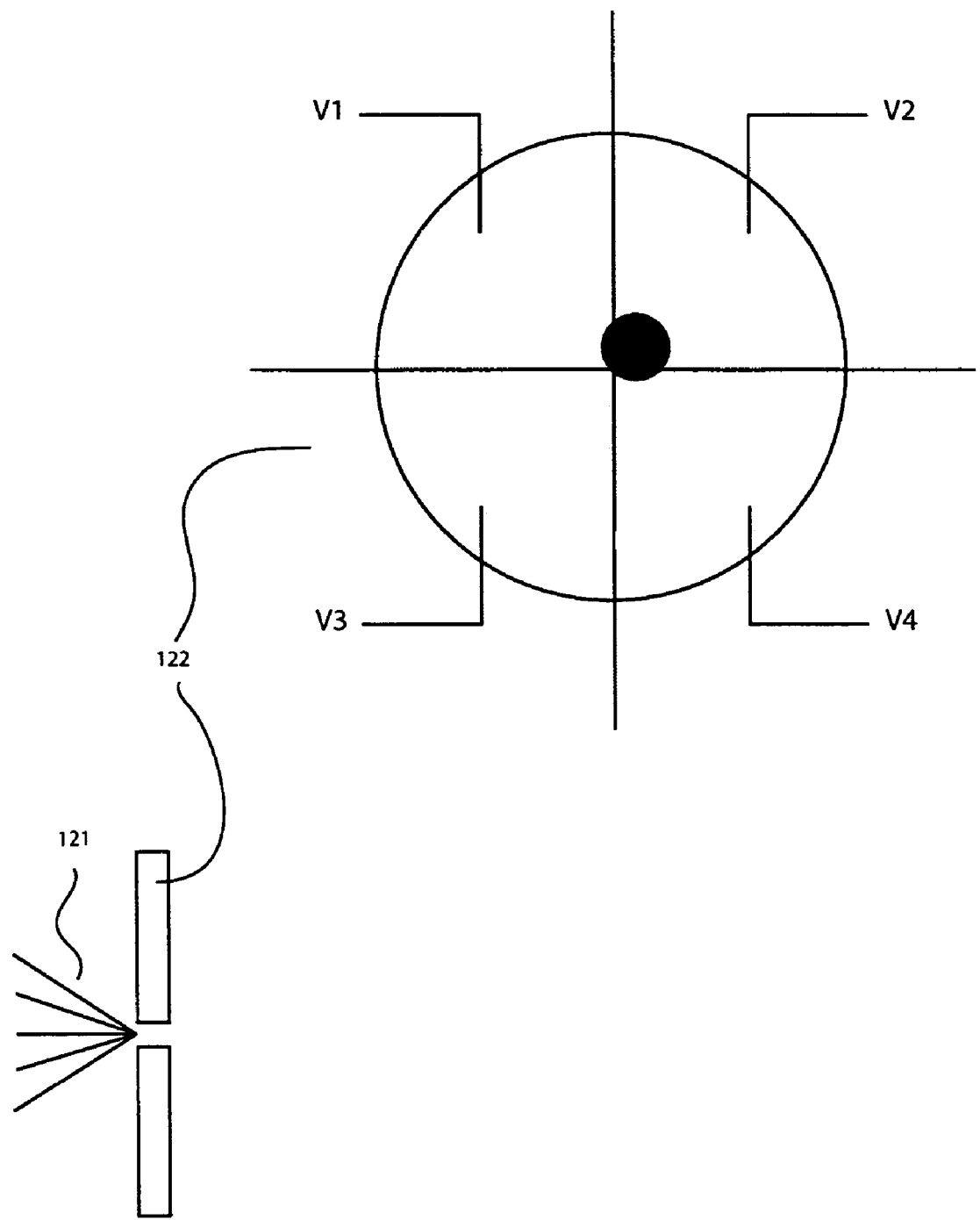
FIG. 13 shows an example of a beam mis-aligned on the center of the quadrant detector. The four voltages generated by the four quadrants can be processed to determine the degree and direction of mis-alignment of the beam and thus the ZMW. The annotations of various components shown in the figure are as follows: 111: ZMW. 112: signal generating molecules. 113: metal film. 114: substrate. 115: objective lens to be aligned. 116: example rays propagating though system. 117: beam splitter/dichroic cube. 118: illumination rays incident. 119: return rays moving toward detector. 120: optional telen lens (used in infinity corrected systems). 121: more rays. 122: photodetector, possibly quadrant photodetector.
Figure 14:
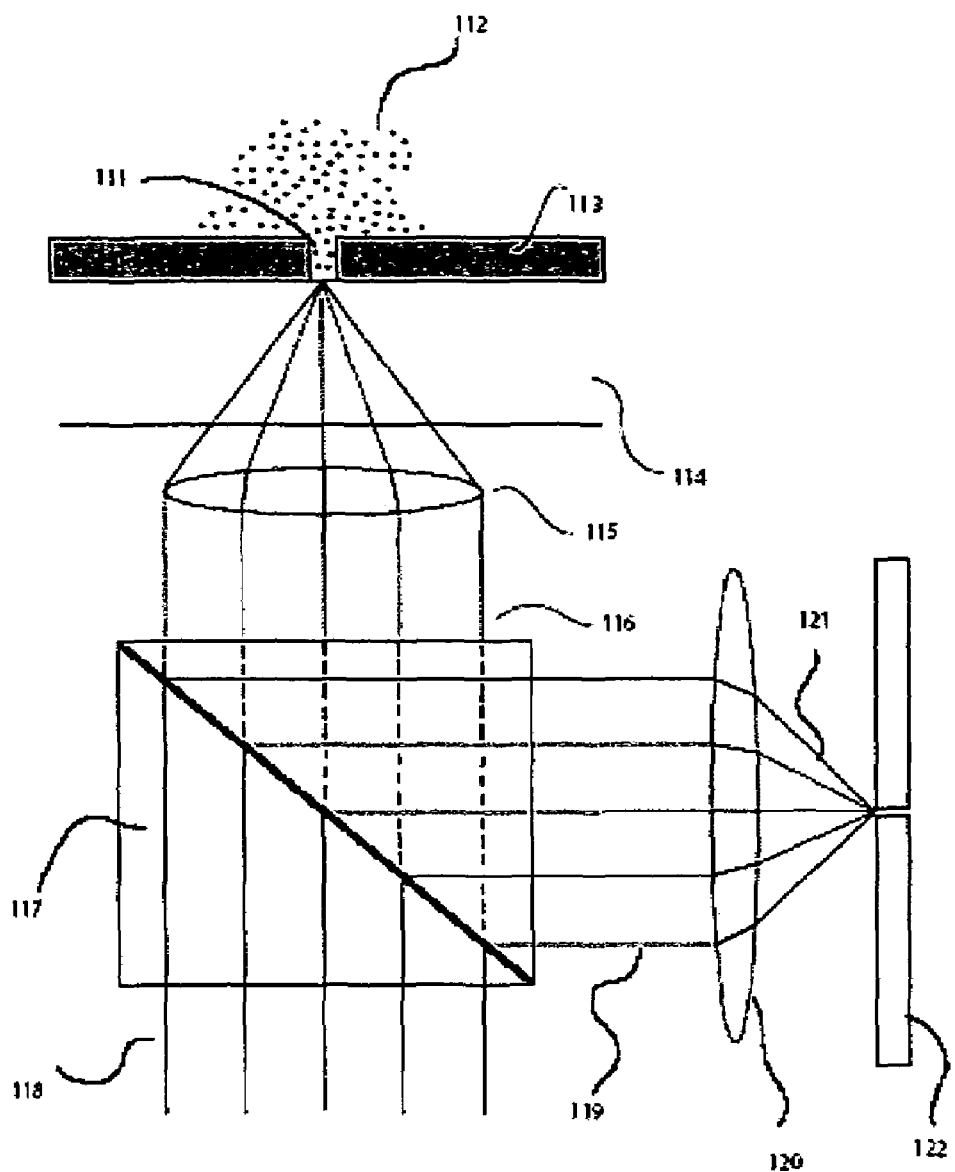
FIG. 14 depicts an alignment strategy that relies on epi-detection rather than trans detection. Second image is inset with front view of quadrant photodiode. The annotations of various components shown in the figure are as follows: 111: ZMW. 112: signal generating molecules. 113: metal film. 114: substrate. 115: objective lens to be aligned. 116: example rays propagating though system. 117: beam splitter/dichroic cube. 118: illumination rays incident. 119: return rays moving toward detector. 120: optional telen lens (used in infinity corrected systems). 121: more rays. 122: photodetector, possibly quadrant photodetector.

Monitoring Enzymatic Synthesis of a DNA Strand by a Single DNA Polymerase Molecule in Real Time In these experiments we sought to track the enzymatic synthesis of a DNA strand by a single DNA polymerase molecule in real time using a fluorescently labeled nucleotide. We immobilized individual Phi29$^{N62D}$ DNA polymerase enzymes (Amersham Biosciences, Piscataway, N.J.) in zero-mode waveguides (ZMWs) by non-specific binding using a dilute enzyme solution. After immobilization, the ZMW structures were washed to remove unbound enzyme, and then exposed to a solution containing the reaction reagents. As for the DNA template, we used a 68-bp pre-primed circular DNA that contained two cytosine bases in characteristic, asymmetric spacing (FIG. 9A). Strand-displacement polymerizing enzymes such as Phi29 DNA polymerase will continuously loop around the circular template and thus generate a long and highly repetitive complementary DNA strand.

We used R110-dCTP (Amersham Biosciences, Piscataway, N.J.) as the fluorescently-tagged nucleotide analog in which the fluorophore is attached to the nucleotide via a linker to the gamma-phosphate. In contrast to the more commonly used base-labeled nucleotide analogs, gamma-phosphate-linked analogs are cleaved through the enzymatic activity of DNA polymerase as the attached nucleotide is incorporated into the growing DNA strand and the label is then free to diffuse out of the effective observation volume surrounding the DNA polymerase. The efficient removal of the fluorophore ensures continuously low background levels and prevents significant interference with DNA polymerase activity. These features of the gamma-phosphate-linked fluorophore are preferable for this application because they will enable replacement of all four bases with fluorophore-tagged analogs, as is generally required for full implementation of the DNA sequencing application. We can distinguish binding of a nucleotide and its subsequent incorporation into nucleic acid from a mismatch event because the rate constants of these two processes are significantly different, and because nucleotide incorporation involves several successive steps that prevent zero delay time events.

All other nucleotides were supplied without labels. We have established a very effective way of removing any remaining trace amount of native dNTP in a nucleotide analog preparation to ensure that errors are not introduced due to the incorporation of unlabeled dNTPs by an enzymatic purification using an alkaline phosphatase prior to the polymerization assay.

To investigate the speed and processivity of the Phi29$^{N62D}$ DNA polymerase under these conditions, we measured incorporation characteristics using R110-dCTP completely replacing dCTP in the reaction mixture, both in solution and with enzyme immobilized on a glass surface. We found that the enzyme efficiently utilizes this analog, synthesizing complementary DNA of many thousands of base pairs in length without interruption in a rolling circle synthesis protocol, using both small preformed replication forks (FIG. 9A) as well as larger circular DNA such as M13 DNA. Similar experiments demonstrated that DNA polymerase can be immobilized to the bottom of ZMWs without loosing this catalytic activity.

We tracked the incorporation of the fluorescently labeled dCTP nucleotide during rolling-circle DNA synthesis by recording the fluorescent light bursts emitted in an individual ZMW. DNA polymerase activity was observed in many waveguides as distinct bursts of fluorescence, lasting for several minutes. The fluorescence time trace showed a characteristic double burst pattern (FIG. 9B), each burst corresponding to an incorporation event of a R110-dCTP analog into the DNA strand and subsequent cleavage of the fluorophore. In histograms of burst intervals derived from the full time trace, two peaks corresponding to DNA synthesis along the short (14 bases, approximately one second) and long (54 bases, approximately four seconds) DNA template segments are visible, consistent with an overall average speed measured in bulk solution under these conditions of approximately ten base pairs per second.

It is noteworthy that we could observe this single-molecule activity at a fluorophore concentration of 10 µM. In conventionally created excitation volumes, the number of fluorophores would be far too high to permit the observation of individual enzymatic turnovers of DNA polymerase. These experiments thus confirmed the validity of the ZMW-based single-molecule DNA sequencing approach by verifying that (a) immobilization of DNA polymerase in ZMWs does not affect its enzymatic activity; (b) fluorescent gamma-phosphate-linked nucleotide analogs do not inhibit the activity of DNA polymerase; and (c) ZMWs provide an adequate degree of confinement to detect single-molecule DNA polymerase activity at physiological concentrations of reagents. More generally, these results prove that ZMWs allow single-molecule analysis of enzyme kinetics, especially involving any enzyme that can be attached to the surface and for which substrates can be fluorescently labeled.

What is claimed is:

1. A substrate comprising:
   an array of a plurality of optical confinements, wherein each of the plurality of optical confinements comprises a core disposed within a cladding layer that is configured to preclude propagation of electromagnetic radiation through the core, and wherein each core is structured to receive reactants; and
   wherein the plurality of optical confinements having a density of greater than $4 \times 10^4$ confinements per mm$^2$ are aligned upon the substrate in at least a first row or a first column, wherein said first row or said first column is aligned along at least a first axis of the substrate.

2. The substrate of claim 1, wherein the plurality of optical confinements are present on the substrate at a density of at least $8 \times 10^4$ confinements per mm$^2$.

3. The substrate of claim 1, wherein the plurality of optical confinements are present on the substrate at a density of at least $1.2 \times 10^5$ confinements per mm$^2$.

4. The substrate of claim 1, wherein the array of optical confinements comprises at least 2 rows of optical confinements.

5. The substrate of claim 1, wherein the array of optical confinements comprises at least 10 rows of optical confinements.

6. The substrate of claim 1, wherein the array of optical confinements comprises at least 100 rows of optical confinements.

7. The substrate of claim 4, wherein the at least two rows of optical confinements are further aligned along at least a second axis.

8. The substrate of claim 4, wherein the at least two rows of optical confinements are further aligned in columns.

9. The substrate of claim 4, wherein the at least two rows of optical confinements are further aligned in a hexagonal array.

10. The substrate of claim 1, wherein the optical confinements each comprise a core disposed through a cladding layer that is disposed upon a supporting substrate.

11. The substrate of claim 10, wherein the core comprises a hole disposed through the cladding layer.

12. The substrate of claim 10, wherein the cladding layer comprises a metal layer.

13. The substrate of claim 10, wherein the cladding layer comprises one or more material selected from aluminum, antimony, arsenic, beryllium, bismuth, boron, cadmium, calcium, carbon, cerium, chromium, cobalt, copper, gallium, indium, iron, lead, lithium, magnesium, manganese, mercury, molybdenum, nickel, niobium, phosphorus, silicon, silicate, silicon nitride, gallium phosphide, gallium arsenide, vanadium, and zinc.

14. The substrate of claim 12, wherein the metal layer comprises one or more metal selected from aluminum and chromium.

15. An optical system, comprising:
a substrate comprising:
an array of a plurality of optical confinements, wherein each of the plurality of optical confinements comprises a core disposed within a cladding layer that is configured to preclude propagation of electromagnetic radiation through the core, and wherein each core is structured to receive reactants; and
wherein the plurality of optical confinements are aligned upon the substrate in at least a first row or column that is aligned along at least a first axis of the substrate;
an excitation light source positioned to direct excitation light at the array of optical confinements; and
a charge coupled device (CCD) positioned to detect emitted signals from the array of optical confinements.

16. The optical system of claim 15, wherein the charge coupled device is selected from an electron multiplying charge coupled device and an intensified charge coupled device (ICCD).

17. The optical system of claim 15, further comprising an optical transmission element for directing excitation light at the array of optical confinements and directing emitted light from the array of optical confinements to the CCD.

18. The optical system of claim 15, wherein the array of confinements and the CCD are aligned so that an optical signal from each confinement is directed to a separate photon detector on the CCD.

19. The optical system of claim 17, wherein the CCD is an electron multiplying CCD (EMCCD).

20. The optical system of claim 17, wherein the CCD is an intensified CCD (ICCD).

* * * * *